US012303286B2

(12) United States Patent
Prince et al.

(10) Patent No.: US 12,303,286 B2
(45) Date of Patent: *May 20, 2025

(54) AUTOMATED ALLERGY OFFICE SYSTEM AND METHOD

(71) Applicants: Ty L. Prince, Knoxville, TN (US); Herman J. Novak, Maryville, TN (US)

(72) Inventors: Ty L. Prince, Knoxville, TN (US); Herman J. Novak, Maryville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/786,160

(22) Filed: Jul. 26, 2024

(65) Prior Publication Data

US 2024/0398329 A1   Dec. 5, 2024

Related U.S. Application Data

(60) Continuation-in-part of application No. 18/445,825, filed on Feb. 22, 2024, and a division of application
(Continued)

(51) Int. Cl.
  *A61B 5/00* (2006.01)
  *G16H 10/60* (2018.01)
  *G16H 20/00* (2018.01)

(52) U.S. Cl.
  CPC ............ *A61B 5/411* (2013.01); *A61B 5/4836* (2013.01); *A61B 5/7445* (2013.01);
(Continued)

(58) Field of Classification Search
  CPC ..... A61B 5/411; A61B 5/4836; A61B 5/7445; A61B 2560/06; G16H 10/60; G16H 20/00
(Continued)

(56) References Cited

U.S. PATENT DOCUMENTS 4,819,657 A   4/1989   Kraft et al.
5,551,441 A * 9/1996   Pitesky ............... A61B 17/205
                                                600/556
(Continued)

FOREIGN PATENT DOCUMENTS

WO   WO2017044691   3/2017

OTHER PUBLICATIONS

U.S. Appl. No. 18/040,762, filed Sep. 7, 2023, Ryan T. Lewinson et al.
(Continued)

*Primary Examiner* — Alex M Valvis
*Assistant Examiner* — Chanel J Jhin

(57) ABSTRACT

The augmented-reality automated allergy office method comprises initially delivering a trace amount of a first allergen to a first test site via a multiple test applicator as the multiple test applicator delivers a trace amount of a second allergen to a second test site during allergen deposition. The multiple test applicator is cooperatively engageable with a fluid tray during allergen loading and with the patient's skin during allergen deposition. Then, capturing a first image of the first and second test site using a smart phone or tablet computer. Subsequently, capturing a second image of the first and second test site within 15 to 20 minutes after allergen deposition. And finally, developing a computer-generated treatment plan using machine learning for the patient with an allergy condition that is a step-by-step procedure, the computer-generated treatment plan being stored in a medical database for treating patients with the allergy condition.

24 Claims, 18 Drawing Sheets

Related U.S. Application Data

No. 18/078,856, filed on Dec. 9, 2022, now Pat. No. 11,911,172, and a continuation-in-part of application No. 17/992,125, filed on Nov. 22, 2022, now Pat. No. 11,696,722, and a continuation-in-part of application No. 17/468,132, filed on Sep. 7, 2021, now Pat. No. 11,369,782, and a continuation-in-part of application No. 17/402,413, filed on Aug. 13, 2021, now Pat. No. 11,517,249.

(52) U.S. Cl.
CPC .......... *A61B 2560/06* (2013.01); *G16H 10/60* (2018.01); *G16H 20/00* (2018.01)

(58) Field of Classification Search
USPC ........................................................ 600/556
See application file for complete search history.

(56) References Cited

U.S. PATENT DOCUMENTS

| | | | |
|---|---|---|---|
| 11,517,249 B2* | 12/2022 | Prince | A61B 5/411 |
| 11,696,722 B2* | 7/2023 | Prince | A61M 37/00 |
| | | | 600/556 |
| 11,911,172 B2* | 2/2024 | Prince | A61B 5/411 |
| 2023/0277119 A1* | 9/2023 | Lewinson | G16H 40/63 |
| | | | 600/306 |

OTHER PUBLICATIONS

U.S. Appl. No. 15/379,276, filed Jun. 22, 2017, Neil Smith.
U.S. Appl. No. 14/775,706, filed Jan. 28, 2016, Eric R. Daines et al.
U.S. Appl. No. 14/338,106, filed Jan. 22, 2015, Sherwin A. Gilman et al.

* cited by examiner

DETAIL "A"
ALLERGEN LOADING

ALLERGEN DEPOSITION

RELAXED STATE

COMPRESSED STATE

COMPRESSED STATE

DETAIL "B"
ALLERGEN LOADING

RELAXED STATE

COMPRESSED STATE

RELAXED STATE

Multiple Puncture Tester

Applicator Puncture Tip

Skin of Patient
First Photo

Skin of Patient
Second Photo

| SKIN TYPE | TYPICAL FEATURES | REACTION TO SUN |
|---|---|---|
| I | Very pale skin.<br>Light-blue, gray, or green eyes.<br>Red or blond hair. | Burns very easily.<br>Almost never tans. |
| II | Pale pink or beige skin.<br>Blue, gray, green or hazel eyes.<br>Blond or brown hair. | Burns easily<br>Tans with difficulty |
| III | Pink or medium-beige skin.<br>Brown or dark-blue eyes.<br>Dark blond, brown, or black hair. | Sometimes burns<br>Tans slowly |
| IV | Olive or light-brown skin.<br>Dark brown eyes. Dark-brown or black hair. | Rarely burns<br>Tans with ease |
| V | Deep dark-brown skin.<br>Very dark, almost black eyes.<br>Black hair. | Almost never burns<br>Tans readily and profusely |
| VI | Medium to dark-brown skin.<br>Dark brown eyes.<br>Dark brown or black hair. | Burns very rarely<br>Tans readily |

Fig. 15
Fitzpatrick Skin Tone Scale

AUTOMATED ALLERGY OFFICE SYSTEM AND METHOD

CROSS-REFERENCE TO RELATED APPLICATIONS

This is a continuation-in-part application and claims priority to U.S. patent application Ser. No. 18/445,825 entitled "Automated Allergy Office System and Method" (Prince and Novak) filed on 2024 Feb. 22; and a divisional application and claims priority to U.S. patent application Ser. No. 18/078,856 entitled "Automated Allergy Office System and Method" (Prince and Novak) filed on 2022 Dec. 9, now U.S. patent Ser. No. 11/911,172 issued on 2024 Feb. 28; and a continuation-in-part application and claims priority to U.S. patent application Ser. No. 17/992,125 entitled "Methods for Administering Multiple Allergens" (Prince) filed on 2022 Nov. 22, now U.S. patent Ser. No. 11/696,722 issued on 2023 Jul. 11; and a continuation-in-part application and claims priority to U.S. patent application Ser. No. 17/468,132 entitled "Multiple Test Applicator" (Prince) filed on 2021 Sep. 7, now U.S. Pat. No. 11,369,782 issued on 2022 Jun. 28; and a continuation-in-part application and claims priority to U.S. patent application Ser. No. 17/402,413 entitled "Multiple Allergen Test Method Applicator" (Prince) filed on 2021 Aug. 13, now U.S. patent Ser. No. 11/517,249 issued on 2022 Dec. 6; and a continuation-in-part application and claims priority to U.S. Provisional Application No. 63/289,350 entitled "Automated Allergy Office System and Method" (Prince) filed on 2021 Dec. 14.

FIELD OF THE INVENTION

The present invention relates to allergy testing, and more particularly to computer-based assessment of allergy skin results in a minimally invasive manner. The present invention also uses artificial intelligence and augmented reality to guide medical professionals to perform their testing and injection duties with significantly fewer mistakes.

BACKGROUND OF THE INVENTION

To avoid an allergic reaction, people need to know what a patient is allergic to. Skin testing is one way a doctor can check on what causes your symptoms. These tests use extracts (a concentrated liquid form) of common allergens such as pollen, mold, dust mites, animal dander, and foods. Once those get under the skin of the patient, they could trigger a reaction called a wheal and flare. An allergy may trigger an itch, like a mosquito bite. That reaction is how the doctor can tell a patient's allergies. When a patient has an allergy, the patient's immune system will make antibodies and set off chemicals to fight off the trigger. That reaction is how a doctor can identify specific allergies of a patient. When a patient has an allergy, the patient's immune system will release chemical mediators in response to the allergy trigger.

The prior art describes allergy testing systems that are burdensome and add complicated steps to the process of patient analysis and treatment.

- U.S. Patent Document No. 20170177802 (Smith) depicts an allergy service management portal including systems, programs, and methods for an allergy management system. In general, the allergy management system provides a system through which a user may manage allergy-related care for one or more patients. In one embodiment, the allergy management system includes an application executed on a computing device, such as a tablet or other type of mobile computing device, which provides an interface for the user to manage various information and/or algorithms to aid the practitioner in providing the allergy care.

- U.S. Patent Document No. 20160026765 (Daines; et al.) depicts an immunotherapy system and method. One aspect of the system and method involves the system generating a patient specific immunotherapy treatment recommendation that includes a network interface configured to receive a first input, second input and third input. A first input includes information having characteristics indicative of a patient's medical history, a second input includes information having characteristics indicative of one or more science factors, and a third input includes information having characteristics indicative of a patient's immune response to one or more antigens of a test.

- U.S. Patent Document No. 20150025412 (Gillman et al.) depicts an allergy skin testing kit. The kit includes a template having puncture site indicators and a computer-readable storage medium storing allergy test information that associates the puncture site indicators of the template with template locations or test substance indicators. A method of performing an allergy skin test includes providing a template having puncture site indicators. Allergy test information that associates the puncture site indicators of the template with template locations or test substances identifiers is obtained. Image data corresponding to a test area on the skin of a test subject obtained and image regions corresponding to the puncture site indicators of the template are identified. Test results corresponding to the image regions are determined based, at least in part, on the allergy test information.

- U.S. Pat. No. 4,819,657 (Kraft, et al.) depicts an automatic allergy testing system. The system includes an electrode capable of testing up to eight different allergies and an associated electronic unit. The electrode includes apparatus to deliver an allergen to the patient without puncturing the patient's skin. The electrode also includes a temperature sensor for sensing the skin temperature in the area surrounding the delivery of the allergen. Electronic apparatus is provided for processing the sensed temperature and storing data related thereto for subsequent print out to an output device. The allergy testing system is controlled so that periodic temperature readings are made at 30 second intervals over approximately a 15-minute testing span.

- PCT Application No. PCT/US2016/050876 (Puype) describes systems and methods of providing allergy-related medical services using inventory control methods. Computer-mediated verification of antigens are used in allergy testing and treatment and visual matching of materials to virtual representations of the materials. The systems and methods describe allergy test kit preparation, allergy test scoring, penicillin allergy testing, compounding patient immunotherapy vial sets, recording immunotherapy progress, and other administrative processes.

Recent technological breakthroughs in the areas of computer software, augmented reality displays, identification tagging and labeling, multiple allergy testing systems, home health care, skin testing and others require that some testing practices be re-examined to confirm that best practices are being effectively used.

What is needed is an allergy testing system and method that uses the power of electronics, software, databases, computer learning, multiple allergy testing systems, augmented reality display technology, electronic displays and computer systems, overlaid on top of improved manual systems, to minimize false positives or negatives, to improve the patient experience, and to reduce the cost of the current manual process and speed the billing process.

What is needed is an allergy testing system and methods using computer software to develop the best possible treatment plan for a patient, and to override the computer generated treatment plan when medical experience indicates that such action is necessary to provide the best possible treatment plan for this patient using machine learning to improve subsequent diagnostic and treatment procedures either for the patient or for other patients with similar allergy issues.

Therefore, there is a need for an allergy testing system and method that is minimally invasive, and which causes minimal discomfort to the patient, which can be initiated and periodically updated either remotely or in the allergist's office, which provides improved accuracy, reduces false positives and false negatives, which is cost-effective, and which is easy to use and manufacture.

What is also needed is an allergy testing system and method that minimizes the opportunity for errors in the complicated systems of testing, analyzing, and treating a patient with allergies.

The objective of the automated allergy office of the present invention is to create systems and methods which combine the most advanced electronics, databases, augmented reality headset, displays, software, apps, tablets and smart phones, that can be layered onto an improved manual system to minimize errors, improve the experience for the patient, resulting in cost savings for the doctor and the patient and to take the initial steps in moving a portion of the testing to the patient's home.

SUMMARY OF THE INVENTION

The automated allergy office of the present invention addresses the needs and the objectives outlined above.

The automated allergy office system of the present invention comprises an augmented reality system, a multiple allergen testing system, and a software system. The augmented reality system is used to select a test site upon the skin of the patient that is relatively clear of discolorations, blemishes, and tattoos. The multiple allergen testing system includes a multiple test applicator cooperative engageable with a fluid tray. The multiple test applicator delivers trace amounts of individual allergens into a plurality of individual locations proximate to the test site under the skin of the patient. The software system provides the allergy doctor with a software generated treatment plan based upon electronic medical records of the patient in combination with a photograph of the test site taken at least 15 minutes after the allergens have been inserted under the skin of the patient. The software system provides the doctor with an override to the software generated treatment plan that can be used whenever appropriate, the override being used to modify the software generated treatment plan to improve subsequent diagnostics and treatment procedures.

A first preferred embodiment of the automated allergy office system and method of the present invention takes a medical professional through an allergy testing process and a follow-on immunology injection process step-by-step using computer tablets, smart phones, an internal office computer system accessing the Patient's medical records, and an augmented reality headset. The augmented reality headset technology, smart phone or computer tablet and software are layered onto an improved manual system to minimize false positives and negatives, to improve the patient experience, resulting in cost savings for the doctor and patient and enabling portions of the allergy testing to be performed remotely from the office of the allergist, either by the patient or by a trained medical technician. The testing vials, the patient specific immunology vials, and the skin test target tags and the patient, will each preferably deploy either radio frequency ID tags, Bluetooth low energy tags, or near field communication tags.

A second preferred embodiment of the automated allergy office system of the present invention comprises back or arm target stickers used by the software and augmented reality headset, smart phone or computer tablet, as sites such that the system determines target locations of where to perform scratch or injection points, wherein moles, skin tags, pre-existing rash or tattoo, that may yield a false positive or negative, display a message for a medical technician to move the back or arm target sticker to a scratch or injection point away from the mole, skin tag, pre-existing rash or tattoo. If the patient has the mole or skin tag as identified by the software or the augmented reality headset, a second test site is identified. The automated office database is populated with pictures of every known mole, shape and size, as well as a complete set of pictures of every version of skin tags. The database also contains pictures of skin rashes. Tattoos are recognized as continuous patterns of black or colored ink. Each of the pictures and patterns can be recognized on skin with various degrees of pigmentation. The database is originally populated with pictures and data commonly known in the medical industry, however, after each doctor evaluates the software suggestions, the database is updated with the knowledge and judgment of the doctor, therefore a constant learning database is achieved. The second test site reduces the likelihood of false positives and negatives. The automated allergy office system of the present invention may be initiated either in the office of the allergist or remotely. The automated allergy office system of the present invention will be updated after each doctor makes a judgement to accept or reject the software suggested results.

A third preferred embodiment of the automated allergy office system of the present invention including an augmented reality headset, smart phone or computer tablet, that projects target allergen injection/scratch points on the image of the back or arm of the patient relative to the target location wherein if the augmented reality headset, smart phone or computer tablet, detects a mole or skin tag, at the target location, or at any of the projected scratch/injection sites, the target will be moved to avoid the mole or skin tag. The augmented reality headset, smart phone or computer tablet, combined with voice recognition technology interprets spoken commands of a wearer of the augmented reality headset, smart phone or computer tablet. The augmented reality headset, smart phone or computer tablet, reads and records the wheal color, and diameter, and the diameter of the flare. In another preferred embodiment, the augmented reality headset, smart phone or computer tablet, also reads and records an infrared signature of a wheal reaction site and flare reaction site. A second preferred embodiment of the automated allergy office system of the present invention also includes means for retesting negative test results. The retesting of the negative test results is performed using prefilled vials and syringes, wherein the augmented reality headset, smart phone or computer tablet, monitors the content of each vial and instructs the nurse where to perform the subcutaneous retest. Each vial is equipped with an electronic tag that contains information on the vial contents, its temperature history, its expiration date, the volume in the vial, along with other information such as the manufacturer's name and its dilution percentage. This information is programmed into the electronic tag or label, by a trained technician, in the doctor's office.

A fourth preferred embodiment of the automated allergy office system of the present invention comprises software learning of the correct interpretation of wheal, flare, color, and infrared temperature measurement, including grading, the software, through an augmented reality headset, recording each test site to ensure that the interpretation of the injection site is analyzed correctly. Grading is on a 0 to 4 scale that grades the severity of the reaction to the allergen. The augmented reality headset, smart phone or computer tablet, captures an image of a test site immediately after an allergen is administered. The augmented reality headset, smart phone or computer tablet, also captures an image of a test site at about a 15-minute interval after the tests are completed. Since the nurse administering the allergy skin tests will be looking through the augmented reality headset, smart phone or computer tablet, while performing the skin tests, the software system can record the individual times for each test. The automated allergy office system of the present invention further comprise means for updating software models of wheals and flairs either by doctors based on industry papers and reports or through the process of the doctor correcting the software's interpretation of the wheals, and flairs during the skin testing process. Such updated software models are designed for achieving optimal values while safeguarding patient identity in a database library.

The automated allergy office of the present invention comprises preloaded allergy testing vials, preloaded allergy multiple skin testing trays. (Using the augmented reality glasses, smart phone or computer tablet, the nurse will be assured that she is placing the correct allergen, in the correct well, of each tray), multiple skin test applicators and intradermal testing syringes. It also uses the latest technology for patient data entry (phone or tablet app), identifying a patient (a biometric—such as face, finger, voice, or a combination of thereof), processing the patient when the patient visits the office, the ability for home allergy testing, software system to help to eliminate mistakes in the testing process, inventory, the data recording process, the analysis process, the immunology process and the billing process. This automated allergy office of the present invention eliminates the need to place marks on a patient's back or arm, to identify allergen test sites, it also eliminates the need to put marks on a patients arm or back for subsequent intradermal injection tests performed only if individual tests are negative on percutaneous tests. Since the system has a built-in timer, the nurse will be notified when a user reaches the 15-minute time has elapsed when the scratches or injections were initially applied. This time out period will instruct the nurse to return to the exam room where the positive, negative analysis will be completed. The system is designed to step the nurse or doctor through the allergy testing process and the follow-on immunology injection process with the use of computer tablets, smart phones, an internal office computer system (patient records and billing) and augmenter reality headset.

The automated allergy office system and method of the present invention reads wheal size change, flare size change, wheal, and flare color as well as wheal and flare temperature. Using the traditional method of reading wheal size change and flare size and color, it is difficult to analyze these changes on a person with dark skin or tattoos. By adding wheal and flare color analysis and wheal and flare temperature change, the interpretation of a positive or negative reaction on a patient with a darker skin complexion or with tattoos will be greatly improved.

Still other objectives of the processes for utilizing the automated allergy office of the present invention will become apparent to those skilled in this art from the following description wherein there is shown and described in the preferred embodiment of this invention, simply by the way of illustration of the best modes contemplated for carrying out the present disclosure. As will be realized, the present disclosure is capable of different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

FIG. 15 depicts the "Fitzpatrick Skin Tone Scale" with the six basic skin types, and the Typical Features and the Reactions to the Sun commonly associated with each basic skin type. is a numerical classification schema for human skin color.

DETAILED DESCRIPTION OF THE PREFERRED EMBODIMENTS

Figure 1:
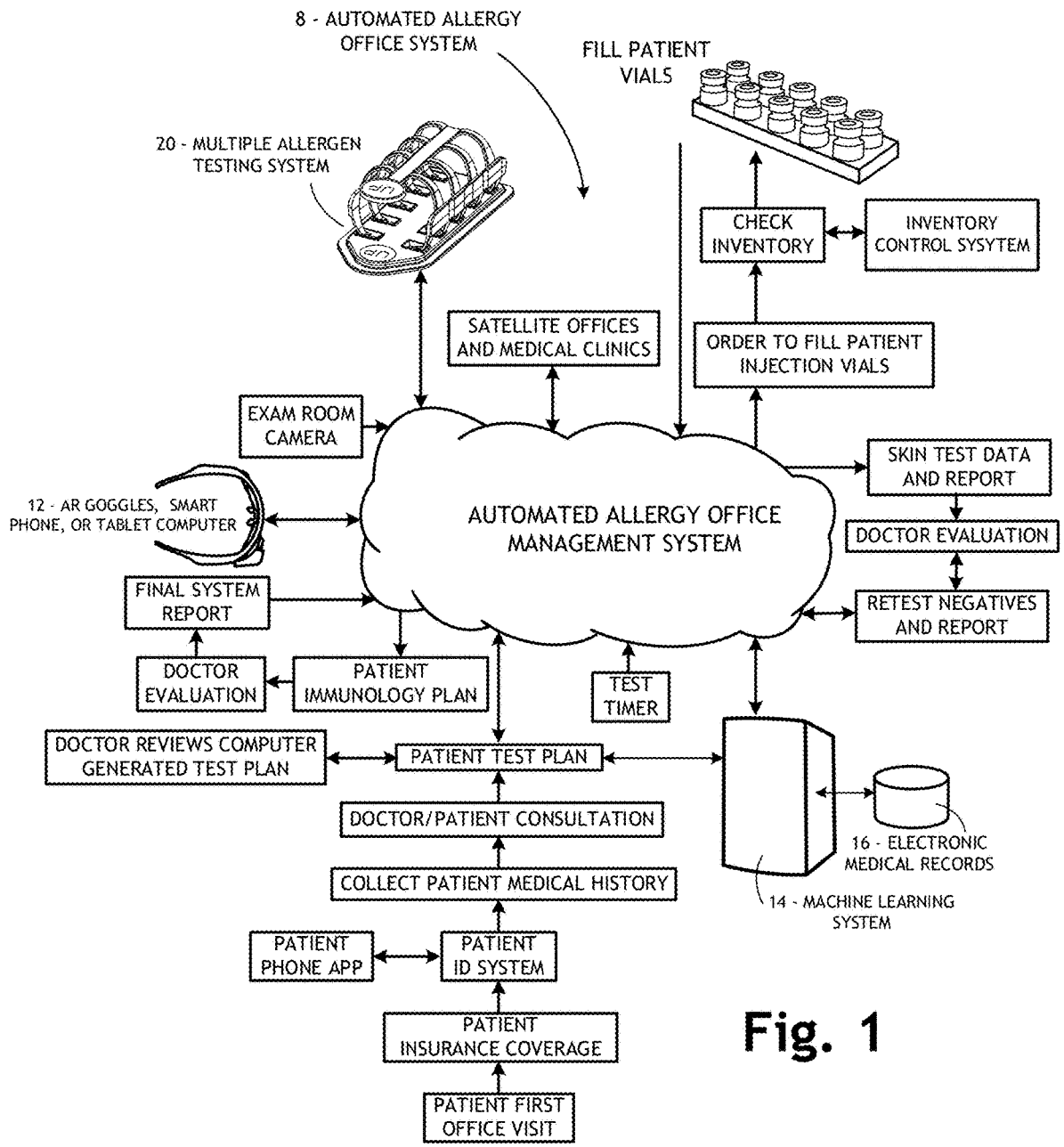
FIG. 1 depicts a first preferred embodiment of the automated allergy office system of the present invention.
Figure 2A:
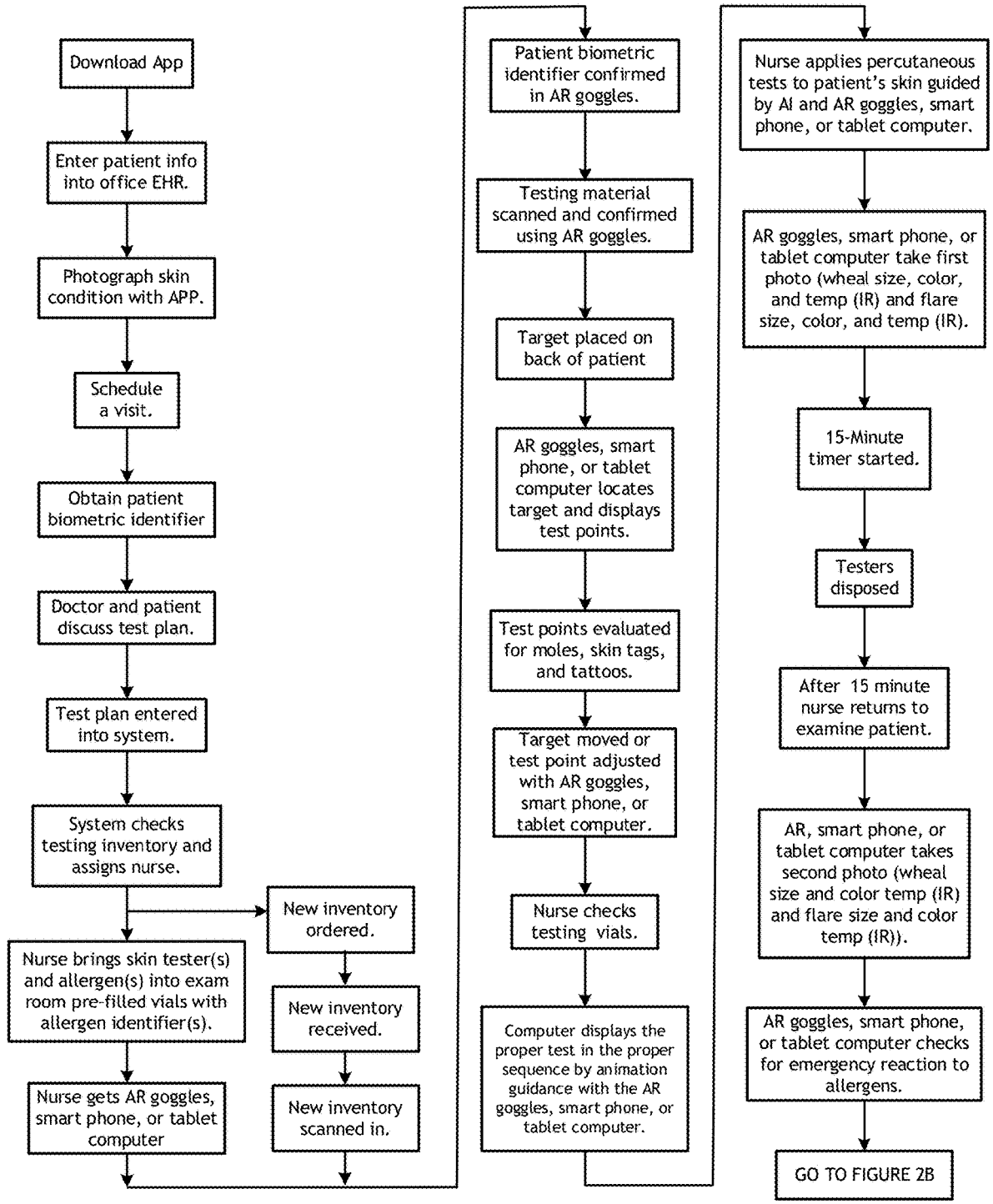
FIGS. 2A, 2B, 2C, and 2D depict the operations performed in the simplified schematic layout of the automated allergy office of the present invention.
Figure 2B:
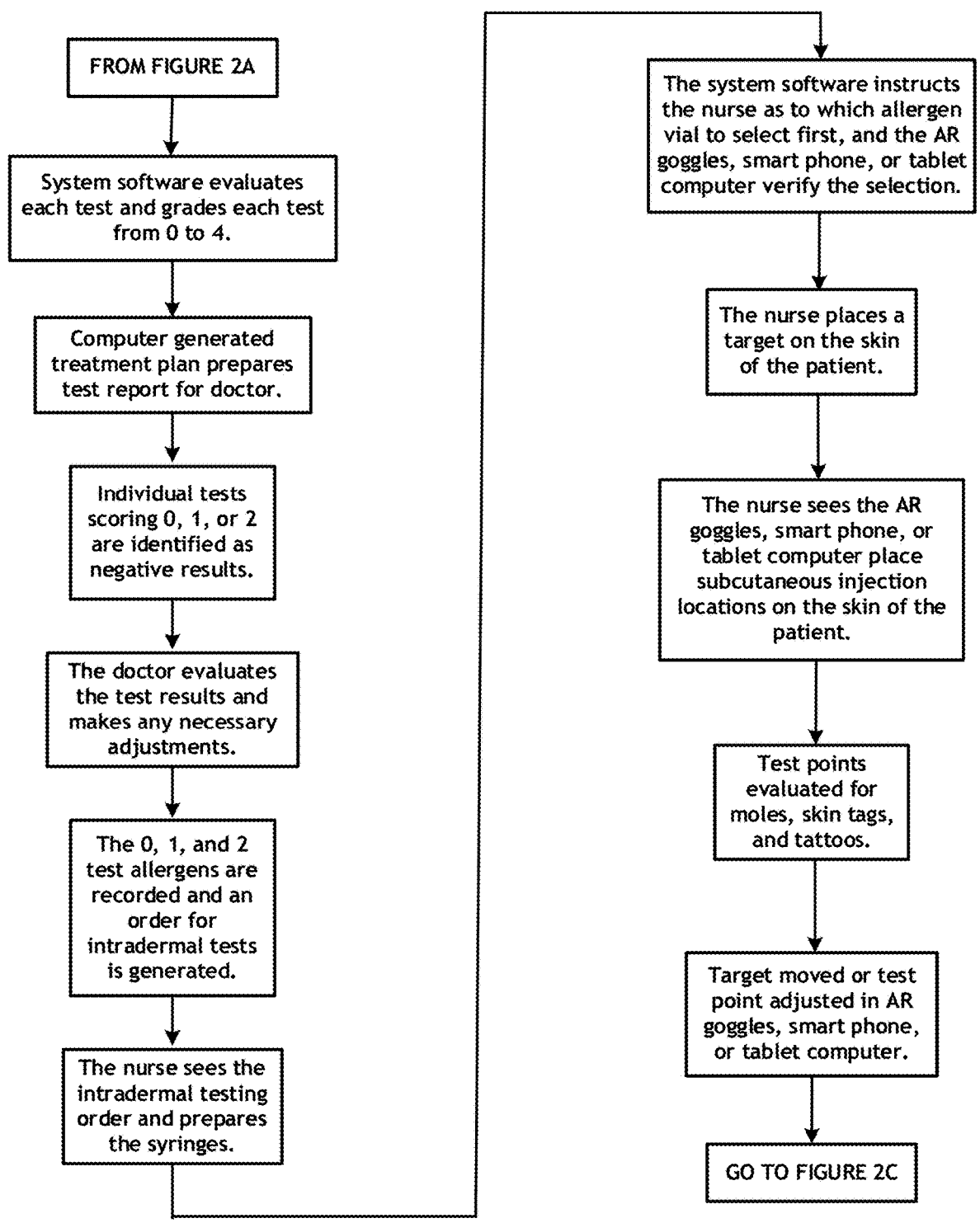
Figure 2C:
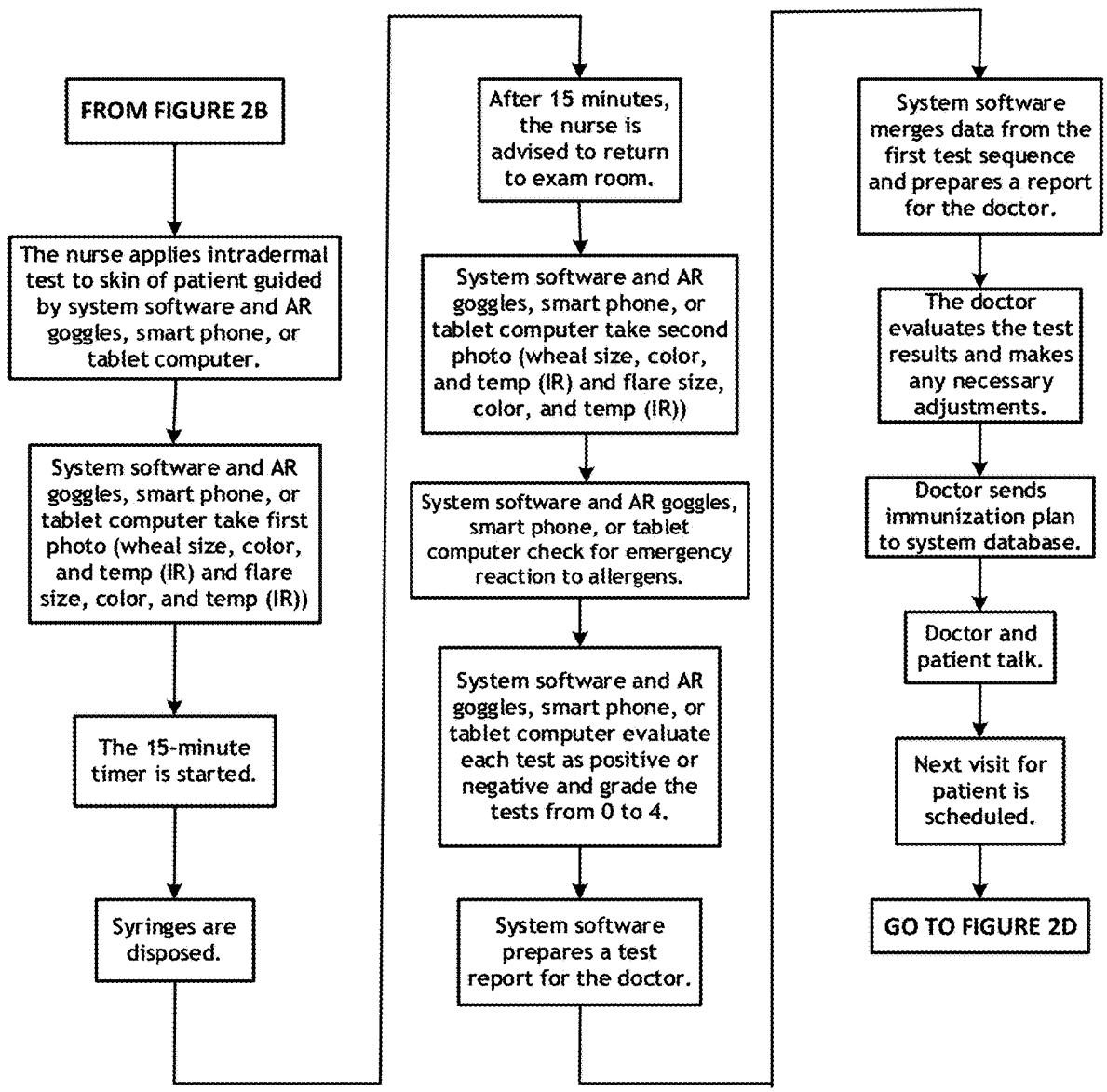
Figure 2D:
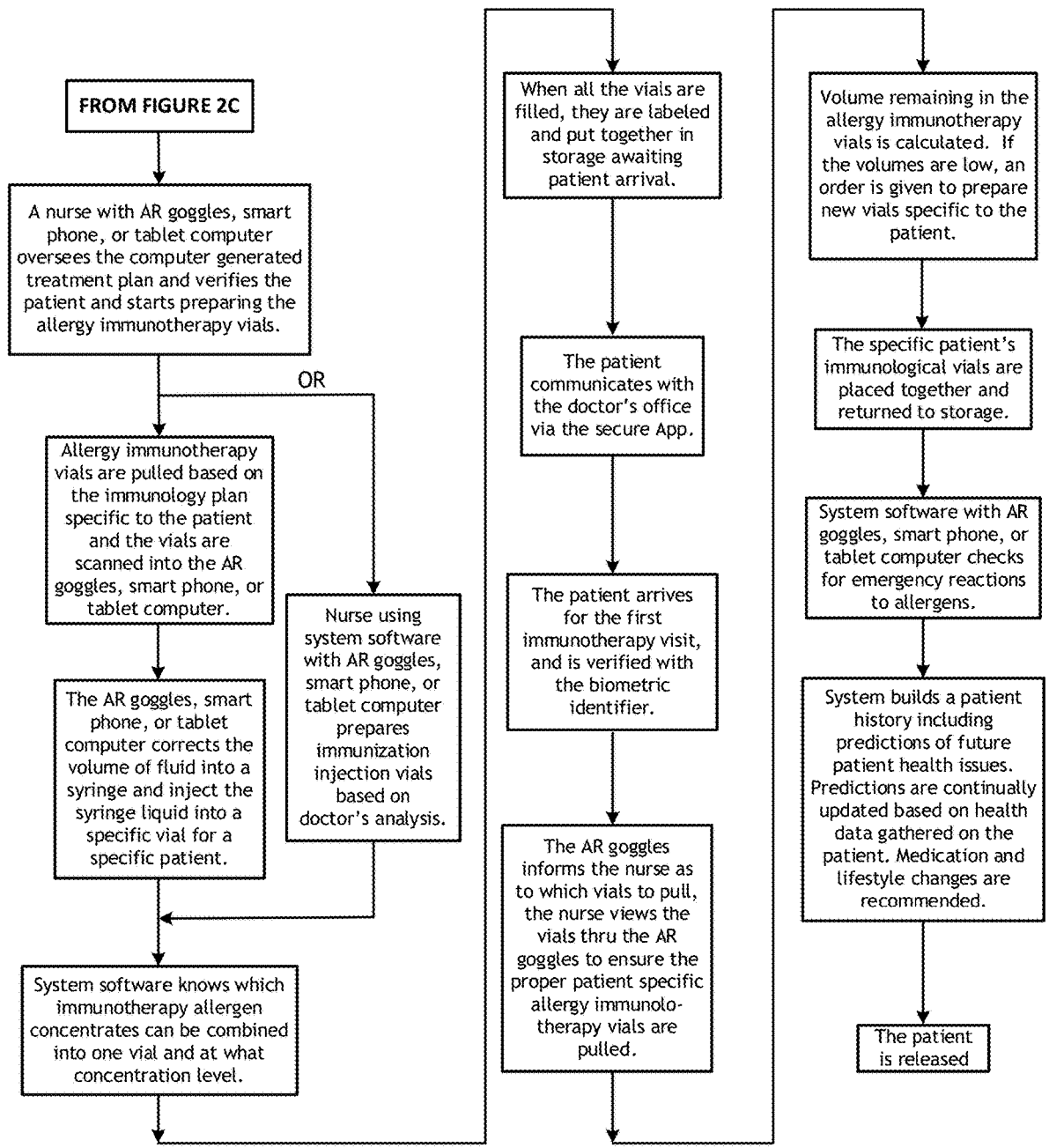

Referring now to the drawings, FIG. 1 depicts a first preferred embodiment of the automated allergy office of the present invention.

In a first preferred embodiment, the automated allergy office system [8] of the present invention is configured to discover and treat one or more allergy issues of a patient. The automated allergy office system [8] comprises a virtual reality viewing device or an augmented reality viewing device [12], a multiple test applicator, and a computer-generated treatment plan for a medical professional treating the patient.

The virtual reality viewing device or augmented reality viewing device [12] selects a first test site and a second test site on skin of the patient. The first and the second test sites are clear of tattoos, moles, birthmarks, and skin rashes.

The multiple test applicator [20] is in cooperative engageable with a fluid tray. The multiple test applicator delivers a small amount of a first allergen to the first test site as the multiple test applicator delivers a small amount of a second allergen to the second test site.

A first allergy condition is detected on the skin of the patient as a first wheal forms at a first test site after fifteen minutes while the first allergen has been delivered into the first test site as a small amount of the second allergen is delivered into a second test site.

Using machine learning [14], the system develops a computer-generated treatment plan for a medical professional to treat the patient. The computer-generated treatment plan is the latest best practice for a patient with the allergy issues of this patient.

The computer-generated treatment plan is developed by the system using machine learning [14]. The computer-generated treatment plan is a step-by-step procedure for a medical professional for treating the patient. The patient's electronic medical record is checked to confirm that the computer-generated treatment plan has not previously been applied to this patient. The computer-generated treatment plan is stored in a medical database for treating the first allergy condition for all patients. The treatment plan not being previously administered to the patient based upon the electronic medical records for the patient.

Figure 4:
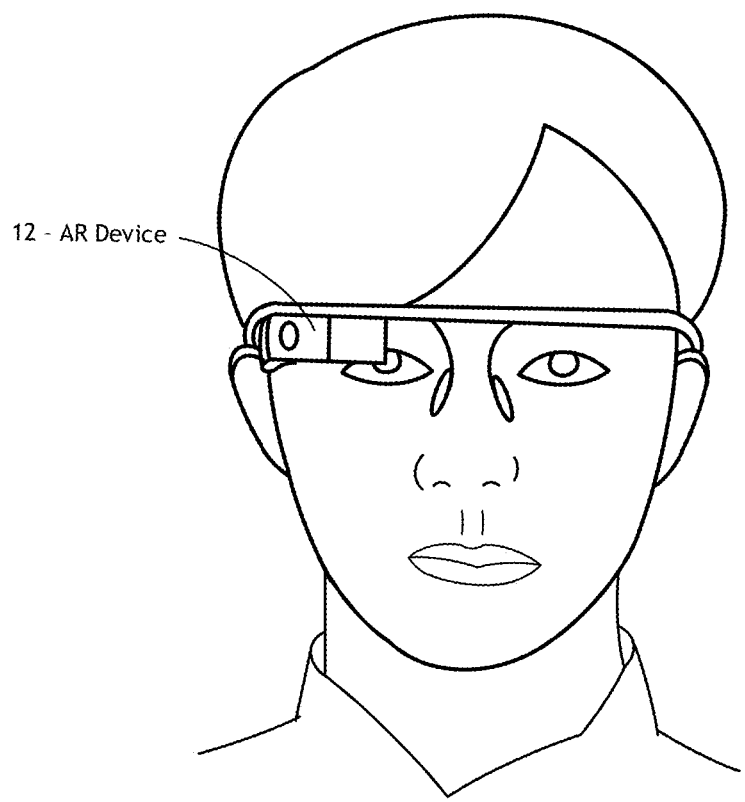
FIG. 4 depicts a medical professional wearing a viewing device for use with the automated allergy system of the present invention.

The automated allergy office system of the present invention [8] comprises an augmented reality system [12], a multiple allergen testing system [10], and a machine learning system [14]. The augmented reality system [12] is used to select a test site upon the skin of the patient that is relatively clear of discolorations, blemishes, and tattoos. As seen in FIG. 4, the multiple allergen testing system [10] includes a multiple test applicator [20] in cooperative engageable with a fluid tray [50]. The multiple test applicator [20] delivers trace amounts of individual allergens into a plurality of individual locations proximate to the test site under the skin of the patient. The machine learning system [14] provides the allergy doctor with a computer-generated treatment plan based upon electronic medical records [16] of the patient in combination a photograph of the test site taken at least 15 minutes after the allergens have been inserted under the skin of the patient. The machine learning system [14] provides the doctor with a manual override to the computer-generated treatment plan which can be used whenever appropriate, the override being used to modify the computer-generated treatment plan to improve subsequent diagnostics and treatment procedures.

A phone or tablet app for the patient is used to input personal and medical information prior to or during the initial office visit. This includes symptoms, photographs of skin rashes with the color of rash and temperature of any rash being recorded, by the App, as part of the patient's record along with any other indications that are unusual or new.

The patient schedules a consultation with the allergist by phone or tablet app. The consultation can either be a visit to the allergist's office, a visit to some other medical facility, or a phone consultation. If the initial visit between the patient and doctor is done remotely, for example, the patient may be home-bound, the skin tests can be performed by a nurse or medical technician from the doctor's office visiting the patient. Similarly, if the patient is home-bound and follow-up testing is required, the tests can be performed by a nurse or medical technician from the doctor's office visiting the patient. Satellite offices and medical clinics can also be incorporated into the system.

The patient's medical history and insurance information is obtained during the initial doctor-patient contact. The medical history may also be submitted by written forms, by phone, or a tablet app or entered by the patient on a website. This includes symptoms, photographs of skin rashes with the color of rash and temperature of any rash being recorded as part of the patient's record along with any other indications that are unusual or new.

Also, one or more of the patient's biometric identifiers are obtained (e.g.—face, finger, voice). Bimodal identification is preferred.

In addition, FIGS. 2A, 2B, 2C, and 2D depict the operations performed in a simplified schematic layout of the automated allergy office of the present invention.

The automated allergy office of the present invention includes safety syringes, single tester, multiple skin testing systems and vials with smart tags or labels. The testing vials, patient specific immunology vials, and skin test target tags, will use the latest ID tag technology.

RFID tags which have an antenna and receives power, via an RF field, generated by the RFID tag reader are used. Bluetooth low energy tags are also used. Near field communication tags are also used. Wiliot provides near field communication tags for the electronic tracking of medication, flexible electronic connectivity, and battery-free sensor tags. These tags enable the electronic tracking and monitoring of medication dispensing and intake.

The Bluetooth low energy tags and the near field communication tags include electronics and memory imbedded in a tag that needs no external power source, it obtains its needed power by harvesting energy from the RF signals that are present in homes and offices, such as WiFi router signals.

A near field communication tag supplied by Wiliot that is glued to a simple antenna printed on plastic or paper can authenticate the proximity of a product by transmitting an encrypted serial number along with weight and temperature data from a device the size of a postage stamp. Eliminating most of the components associated with traditional Bluetooth, these tags lower sale and maintenance costs to previously unachievable levels.

These tags communicate with the office automation system through secure WiFi or even through the augmented reality headset.

The augmented reality headset preferably includes voice recognition that understands the voice of the nurse, will read the color and size of the wheal and flare, and will read the infrared signature of the wheal and flare reaction site.

The driver for the augmented reality headset may be a computer, a tablet, or a secure WiFi network.

The prefilled single tester allergen tray preferably uses a barcode, a QR-type code or some other identifier. The prefilled multiple skin test allergen tray preferably uses a barcode, a QR-type code or some other identifier. Prefilled allergen vials preferably use a barcode, a QR-type code or some other identifier.

The trays are scanned with the augmented reality headset. Even though the trays are preloaded, the augmented reality headset serves to record what was given to the patient.

Back or arm target stickers are used by the machine learning system in combination with an augmented reality headset as a location point such that the system knows where to display the scratch or injection points (moles, skin tags, pre-existing rash or tattoos), that could cause the system to locate a scratch point or an injection point that may give a false positive or negative. A message will display for the nurse to move the target sticker or will automatically move the injection point away from the mole, skin tag, pre-existing rash or tattoo.

The augmented reality headset captures the image of the test sites immediately after each test is completed as well as between 15 to 20 minutes after the tests are completed.

After between 15 to 20 minutes, the nurse returns to the exam room so that the system can perform the final data collection and analysis. It is important to return to the exam room after the 15 to 20-minute interval because some wheal and flare reactions can dissipate quickly after 25 to 30 minutes. An accurate analysis timed after 15 minutes will help to minimize the number of false positives or negatives.

If the machine learning system sees a reaction that may harm the patient, the system signals the medical professional to see the patient immediately. The testing process is timed.

The computer-generated treatment plan uses machine learning. Machine learning algorithms work on the basis that strategies, algorithms, and inferences that worked well in the past are likely to continue working well in the future. Machine learning involves computers learning from data provided so that they carry out certain tasks. For tasks to treat specific allergies, it only becomes necessary to track is effective and what is not.

As the allergy databases improve with input from more practitioners, the solutions provided by the computer-generated treatment plan of the present invention will also improve. A vast amount of data is currently available online for practitioners (see for example "Allergen Online", "Allergen Atlas", "Care Precise", "Contact Allergen Database" to name a few.

A first preferred embodiment of the automated allergy office system and method of the present invention takes a medical professional through an allergy testing process and a follow-on immunology injection process step-by-step using tables, computer tablets, smart phones, an internal office computer system accessing the patient's medical records, and an augmenter reality headset. The augmented reality headset technology and the machine learning are layered onto an improved manual system to minimize false positives and negatives, to improve the patient experience, resulting in cost savings for the doctor and patient and enabling portions of the allergy testing to be performed remotely from the office of the allergist, either by the patient or by a trained medical technician. The testing vials, the patient specific immunology vials, and the skin test target tags, will each preferably deploy either radio frequency ID tags, Bluetooth low energy tags, or near field communication tags.

A second preferred embodiment of the automated allergy office system of the present invention comprises back or arm target stickers used by the machine learning system and the augmented reality headset as sites such that the system determines target locations of where to perform scratch or injection points, wherein moles, skin tags, pre-existing rash, or tattoo, that may yield a false positive or negative display, a message for a medical technician to move the back or arm target sticker to a scratch or injection point away from the mole, skin tags, pre-existing rash, or tattoo is displayed. If the patient has the mole, skin tags, pre-existing rash, or tattoo, as identified by the machine learning system or the viewing device, a second test site is identified. The second test site, with no moles, skin tags, rash, or tattoo, reduces the likelihood of false positives and negatives. The automated allergy office system of the present invention may be initiated either in the office of the allergist or remotely. The automated allergy office system of the present invention may be periodically updated either in the office of the allergist or remotely.

A third preferred embodiment of the automated allergy office system of the present invention including an augmented reality headset that projects target allergen injection points on the image of the back or arm of the patient relative to the target location wherein if the augmented reality headset detect a mole, skin tag, pre-existing rash, or tattoo, the target location is moved to avoid the mole, skin tag, pre-existing rash, or tattoo. The augmented reality headset combined with voice recognition technology interprets spoken commands of a wearer of the augmented reality headset. The augmented reality headset reads and records the wheal color, wheal size and change in color as well as flare size. In another preferred embodiment, the augmented reality headset also reads and records an infrared signature of a wheal reaction site and flare reaction site. A third preferred embodiment of the automated allergy office system of the present invention also includes means for retesting negative test results. The retesting of the negative test results is performed using prefilled vials and syringes, wherein the augmented reality headset monitors the content of each vial.

A fourth preferred embodiment of the automated allergy office system of the present invention comprises machine learning of the correct interpretation of wheal, flare, color, and infrared temperature measurement, including grading, the machine learning through an augmented reality headset, recording each test site to ensure that a serious negative reaction does not occur at the injection site. The augmented reality headset captures an image of a test site immediately after an allergen is administered. The augmented reality headset also captures an image of a test site at between a 15 to 20-minute interval after the tests are completed. The automated allergy office system of the present invention further comprise means for updating the machine learning system models with current values. Such updated models are designed for achieving optimal values while safeguarding patient identity in the machine learning system library.

Still other objectives of the processes for utilizing the automated allergy office of the present invention will become apparent to those skilled in this art from the following description wherein there is shown and described in the preferred embodiment of this invention, simply by the way of illustration of the best modes contemplated for carrying out the present disclosure. As will be realized, the present disclosure is capable of different embodiments, and its several details are capable of modification in various, obvious aspects all without departing from the invention. Accordingly, the drawings and descriptions are to be regarded as illustrative in nature and not as restrictive.

The database and the machine learning system examines the size change of the wheal, the size change of the flare, any color change of the wheal and flare, and infrared measurement of any temperature change.

The machine learning analysis is comprehensive. A printout of analysis of wheals, flares, color, temperature, and grade is provided to the doctor. Paper, tablet, or computer accessible system analyses is provided for the doctor to evaluate and adjust as needed. Negative test results from the percutaneous scratch testing are retested with prefilled vials and syringes (the augmented reality headset reads the content of each vial; the augmented reality headset monitor the injection site).

The verified negatives are recorded and merged with the initial percutaneous allergy test results. If a negative retest shows a positive from the intradermal injection retest, the data is merged with the initial test data for the doctor's analysis and conclusion.

After the doctor adjusts the machine learning system, the data is entered into the patient's record and is used for the automatic preparation of the patient's immunological shot vials.

A copy of this record, with patient-specific data removed, is put into the machine learning system database. This will improve the machine learning system in the future.

For examples of how these technologies have improved current medical diagnosis, see the following references:

U.S. patent Ser. No. 16/939,790 (Chan; et al.) entitled "High Fidelity Clinical Documentation Improvement (CDI) Smart Scoring Systems and Methods" describes a clinical documentation improvement smart scoring method. The method may include predicting, via per-condition diagnosis machine learning models and based on clinical evidence received by a system, a probability that a medical condition is under-documented and, via per-condition documentation machine learning models and based on documentation received by the system, a probability that a medical condition is over-documented.

U.S. patent Ser. No. 11/250,937 (Malvankar; et al.) entitled "System and Method to Share and Utilize Healthcare Data" describes a computer-implemented method, system, and computer program product for sharing and utilizing healthcare data. The program provides one or more computer-implemented machine learning models for analyzing the healthcare data and recording transactions involving the machine learning models using a blockchain as a distributed ledger that is shared, replicated and synchronized. Healthcare data is also used to train the machine learning models.

U.S. patent Ser. No. 16/591,625 (Garcia Santa; et al.) and U.S. patent Ser. No. 16/591,623 (Villazon-Terrazas; et al.) both entitled "Medical Diagnostic Aid and Method" and both assigned to Fujitsu Ltd. describe diagnostic aids, and methods for assisting medical personnel in performing a diagnosis, and computer readable media comprising code which, when executed by a computer, cause the computer to execute a method for assisting medical personnel in performing a diagnosis, wherein the diagnostic aids comprise: a receiver to receive an unstructured input; an analyzer and parser to split the unstructured input into a plurality of logical components, and to detect medical terms in the plurality of logical components; a mapping engine to receive a medical classification hierarchy of medical standard codes in the form of a knowledge graph, and semantically annotate the knowledge graph with synonyms of medical terms used in the medical standard codes; an automatic coding solver to analyze the medical terms detected in the plurality of logical components by the analyzer and parser, to generate a list of potential matching medical standard codes for each of the medical terms, to compare the lists of potential matching medical standard codes, and to output top matching medical standard codes based on the comparison; and an enrichment engine comprising a database of diagnoses linked to symptoms and treatments, wherein the enrichment engine compares the top matching medical standard codes output by the automatic coding solver against entries in the database of diagnoses, and outputs diagnoses, symptoms and treatments linked to each of the top matching medical standards codes for assisting medical personnel in providing a diagnosis.

U.S. patent Ser. No. 16/018,301 (Devarakonda; et al.) entitled "Cognitive Analysis and Disambiguation of Electronic Medical Records for Presentation of Pertinent Information for a Medical Treatment Plan" describes a mechanism provided in a data processing system comprising a processor and a memory. The memory comprises instructions that are executed by the processor to specifically configure the processor to implement a cognitive analysis engine for analysis and disambiguation of electronic medical records for presentation of pertinent information for a medical treatment plan. The cognitive analysis engine receives a medical condition for a current or upcoming interaction with a patient. The cognitive analysis engine receives a medical mental model that emulates the thinking of a medical professional with regards to reviewing a patient's electronic medical records to identify pertinent information for a medical treatment plan to treat the medical condition.

Figure 3:
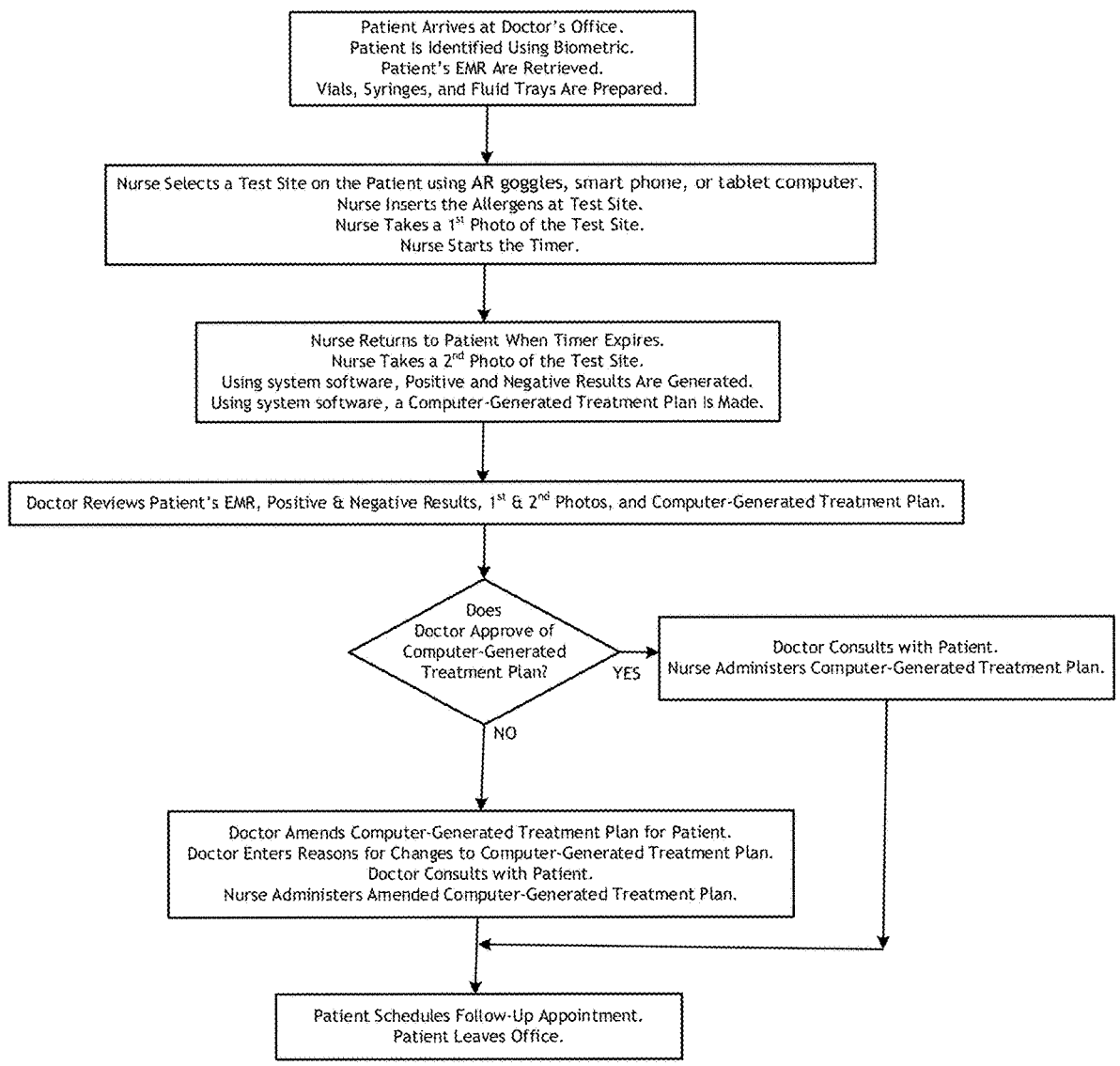
FIG. 3 depicts a simplified logic diagram as to how the software presents to the doctor an action plan based upon the photos of the patient test site, enabling the doctor to override the software's action plan and teach the software that is using the automated office system of the present invention.

FIG. 3 depicts the simplified logic diagram as to how the patient test plan is developed as a cooperative effort between the machine learning system [14] and the physician. The automated allergy office system develops the computer-generated treatment plan based upon the electronic medical records [16] of the patient, the allergen scans and test results, and the best practice and machine learning available. The computer-generated treatment plan is then presented and reviewed by the treating physician. If the treating physician approves and accepts the computer-generated treatment plan, the treating physician then consults with the patient as to the plan going forward for treatment. The computer-generated treatment plan can also predict future medical problems based on the patient's past history of medical conditions and treatments as well as the patient's lifestyle. The physician can then discuss these predictions with the patient and together, they can construct a medical plan and lifestyle changes that can potentially eliminate or reduce the severity of the medical allergy conditions.

If the treating physician opts to modify the computer-generated treatment plan, the changes are entered into the system and the reason for the changes are also entered.

The treating physician also advised the system if the changes are to be made for all patients going forward or if the changes are unique to this patient. In either event, this enables the system to learn using machine learning to improve subsequent diagnostic and treatment procedures either for this patient or for other patients with similar allergy issues. The treating physician then consults with the patient as to the plan going forward for treatment.

Before each shot is given to a patient, the unique patient identifier is checked to confirm patient identity, the patient's vials are scanned, and the injection volume is displayed for the nurse or medical technician. After the shots are given, the vials are scanned again. Finally, the system software, through the augmented reality headset records each shot site to ensure that the patient does not experience a negative reaction to the injection. If the patient complains of a negative reaction, or if the augmented reality headset detects a significant negative reaction, an alert is given to the nurse, medical technician, and the doctor requesting immediate help. The time to administer the immunology shots is also recorded.

As the doctor, nurse, and medical personnel become familiar with the images and animation displayed in the augmented reality headset, he or she can opt to speed up or eliminate portions of the animation. However, the sped-up visuals will continue to display all the key elements of the display sequence to ensure that the proper process and procedure is followed.

As used herein, the term "augmented reality headset" refers to a relatively new technology that integrates information from the real world and the virtual world "seamlessly". Specifically, by means of techniques such as electronic computer processing, augmented reality technology applies virtual information to the real world by simulation and then superimposition, and the result is perceived by human senses. Therefore, a sensory experience that transcends reality is achieved. In this case, the real environment and the virtual object are superimposed in the same picture or space in real time. The augmented reality technology not only displays real-world information, but also displays virtual information at the same time, so that the two kinds of information complement and superimpose each other. In the visual augmented reality technology, the real world and computer graphics are multi-synthesized by using a helmet or AR glasses display. With maturity of the market, a variety of augmented reality products have emerged, particularly head-mounted augmented reality headsets.

U.S. patent Ser. No. 15/129,750 (Badiali; et al.) entitled "Augmented Reality Glasses for Medical Applications and Corresponding Augmented Reality System" filed Mar. 27, 2015.

U.S. patent Ser. No. 17/063,629 (Buras; et al.) entitled "System and Method for Three-Dimensional Augmented Reality Guidance for Use of Medical Equipment" filed Oct. 5, 2020.

The automated allergy office of the present invention will result in portions of the allergy diagnosis and treatment moving out of the allergist's office to intermediate medical sites and to a certain degree of home testing, analysis, and treatment of allergies.

FIG. 4 depicts a medical professional wearing a viewing device [12] for use with the automated allergy office system of FIG. 1. The viewing device enables the medical professional to view the computer data while making eye contact with the patient.

Figure 5:
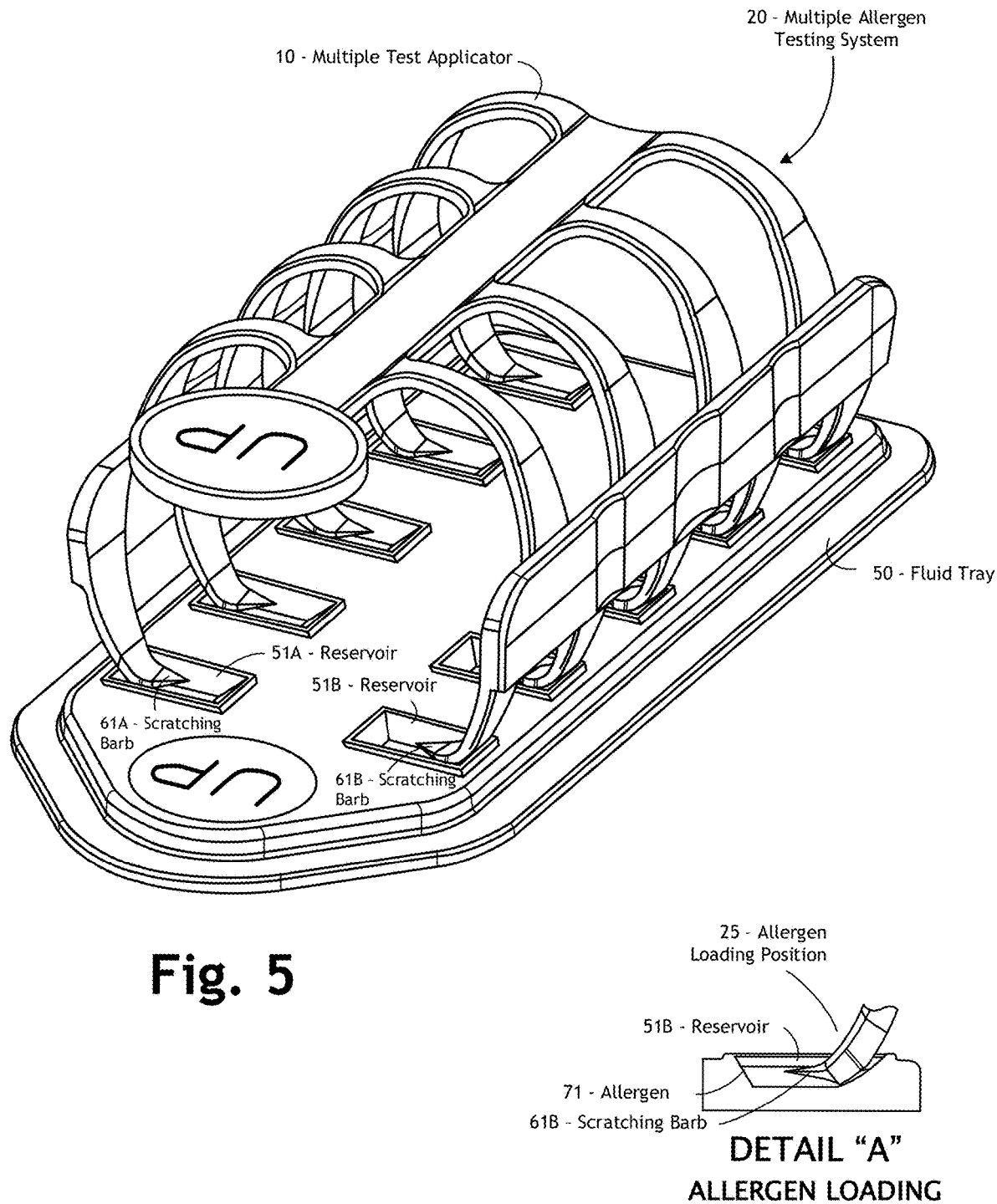
FIG. 5 depicts an assembly view of a first preferred embodiment of the multiple allergen testing system for the automated allergy office of the present invention comprising a first preferred embodiment of the multiple test applicator having ten applicators cooperatively engaged with a fluid tray, the multiple test applicator being disposed on the fluid tray; and DETAIL "A" depicting an exploded side view of the scratching barb projecting upward relative to the fluid tray disposed in a reservoir of the fluid tray during allergen loading, the reservoir being partially filled with an allergen.

FIGS. 5 through 12 depict a unique "scratch tester". FIG. 5 depicts an assembly view of a first preferred embodiment of multiple allergen testing system [20] comprising of a first preferred embodiment of the multiple test applicator [10] including a first scratching barb [61A] in cooperative engagement a first fluid reservoirs [51A] and a second scratching barb [61B] in cooperative engagement with a second fluid reservoir [51B] both fluid reservoirs [51A and 51B] positioned in a fluid tray [50].

DETAIL "A" depicts an exploded side view of the scratching barb [61B] positioned in a reservoir [51B] of the fluid tray [50] while in the allergen loading position. The reservoir [51B] is partially filled with allergen [71]. Here, the scratching barbs [61A and 61B] project in a downward direction pointing to the bottom of the fluid tray [50]. The multiple test applicator [10] is enabled to reposition from the compressed state to the relaxed state when placed on the skin of the patient [80] during allergen deposition [92].

A first scratching barb [61A] is in cooperative engagement with a first reservoirs [51A] of a fluid tray [50], and a second scratching barb [61B] is in cooperative engagement a second reservoir [51B] of the fluid tray [50]. The fluid tray is shown in FIG. 3. Each reservoir preferably retains a different liquid for skin testing.

When allergens are placed into respective reservoirs [51A and 51B] in the fluid tray [50], care is taken to avoid using excess amounts of the allergens [71] which may cause cross contamination of allergens. The size of the reservoirs and the distance between adjacent reservoirs are designed to minimize any cross contamination of the allergens.

Figure 6:
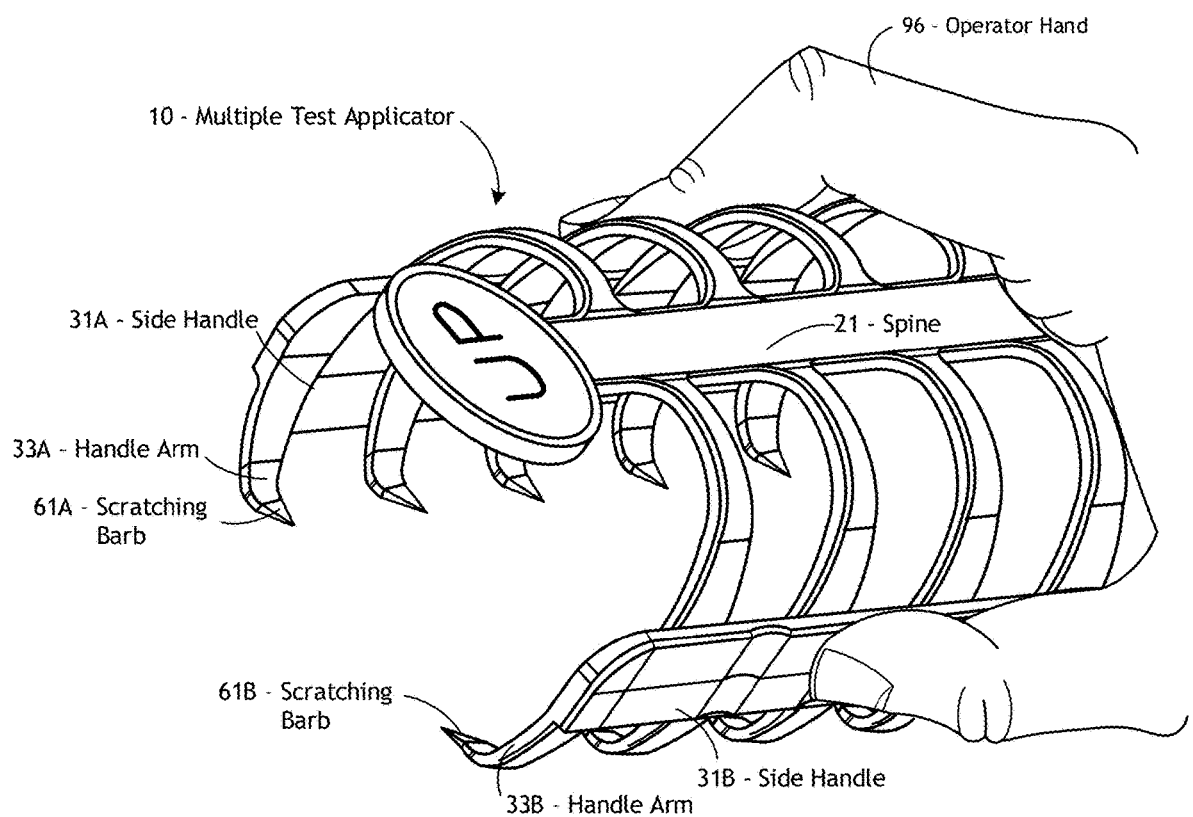
FIG. 6 depicts the multiple test applicator of FIG. 5 held in one hand by an operator, with the thumb positioned on a first finger grip on a first side frame and the index finger of the same hand positioned on an opposing finger grip on an opposing side frame, the first side frame opposing the second side frame.

FIG. 6 depicts the first preferred embodiment of the multiple test applicator [10] held in one hand by a medical technician, with the thumb positioned on a first finger grip [35A] on a first side handle [31A] and the index finger of the same hand positioned on a second finger grip [35B] on a second side handle [31B], the first side handle [31A] opposing the second side handle [31B].

The multiple test applicator [10] is in the relaxed state while in allergen loading position [25] when the multiple test applicator [10] is in cooperative engagement with the fluid tray [50]. The multiple test applicator [10] is preferably sized to be held in one hand of a medical technician administering the allergen skin testing. The pair of finger grips [35A and 35B] are positioned on opposing sides of each opposing side handle [30 and 31]. The medical technician grasps the applicator [10] by the pair of opposing finger grips [35A and 35B] in her hand during the allergen loading process and the allergen depositing process by placing her thumb on one finger grip [35A] and her forefinger of the same hand on the other finger grip [35B]. The applicator involves one hand of an operator [96] positioning a multiple test applicator [10] onto a loading tray [50] during the allergen loading.

The use of the finger grips [35A and 35B] to move the multiple test applicator [10] from the relaxed state to the compressed state and then back again to the relaxed state enables one-handed operation by the operator.

Multiple allergens are retainable in the reservoirs [51A and 51B] of the fluid tray [50]. Allergens are initially selected and placed into the individual containment reservoirs [51A and 51B] of the fluid tray [50], and care is taken not to use an excess amount of the allergens. The multiple test applicator [10] has multiple scratching barbs [61A and 61B]. During the allergen loading each scratching barb [61A or 61B] is positioned in a reservoir [51A or 51B] containing an allergen [71].

Figure 7:
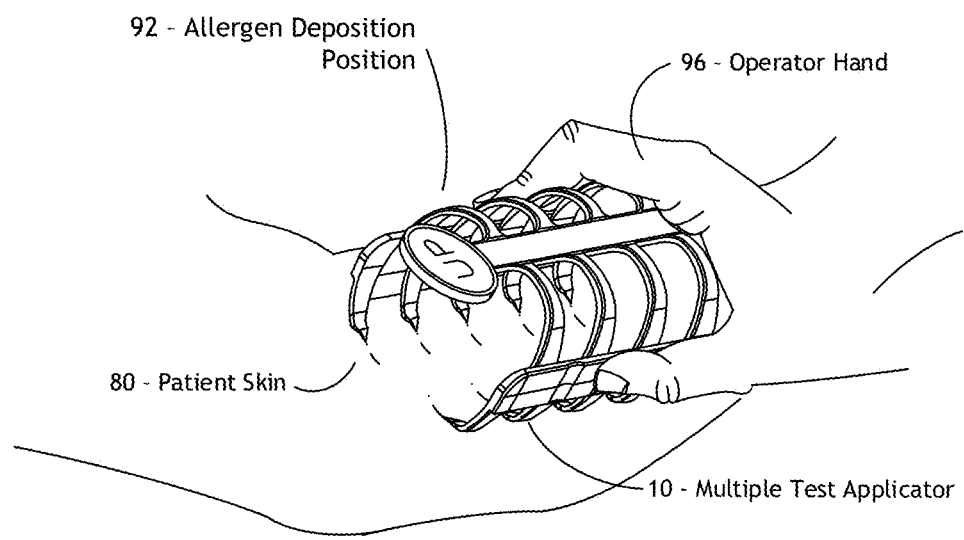
FIG. 7 depicts the multiple test applicator of FIG. 5 held in one hand by an operator during allergen deposition as the allergens are deposited under the skin on a forearm of a patient.

FIG. 7 depicts the multiple test applicator [10] held in one hand of the medical technician as the allergens are deposited under the skin on a forearm of a patient [80].

The operator [96] using one hand then repositions the multiple test applicator [10] onto the skin of the patient [80] for allergen deposition [92].

During allergen deposition [92], the medical technician uses the same hand as in the allergen loading enabling one-handed operation throughout the entire process. The first scratching barb [61A] facilitates a first scratch on a first epidermis layer of the patient while in the during allergen deposition [92] relative to the skin of the patient [80]. The second scratching barb [61B] facilitates a second scratch on a second epidermis layer of the patient during allergen deposition [92] relative to the skin of the patient [80].

After being repositioned from the barb allergen loading position [25] once the first and scratching barbs are loaded with some of the allergens. The multiple test applicator [10] is primed to deposit the allergens in the scratches on the skin of the patient [80].

Figure 8A:
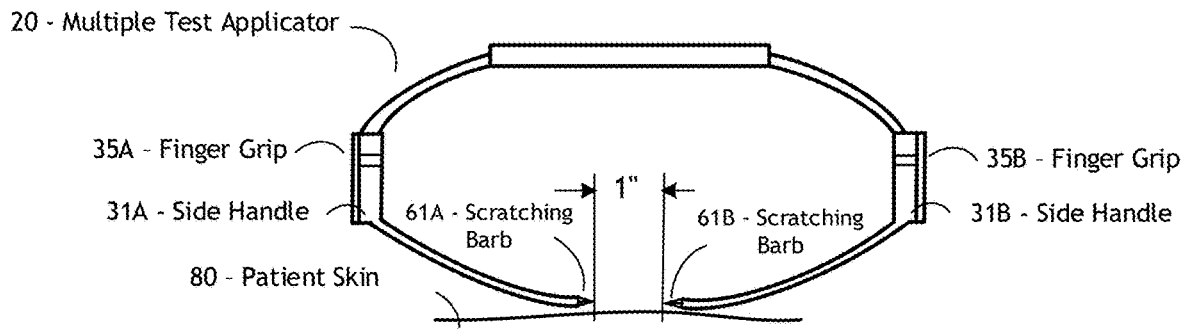
FIG. 8A is a front view of the multiple test applicator of FIG. 5, the multiple test applicator being in a relaxed state, the scratching barbs resting upon the skin of the patient.
Figure 8B:
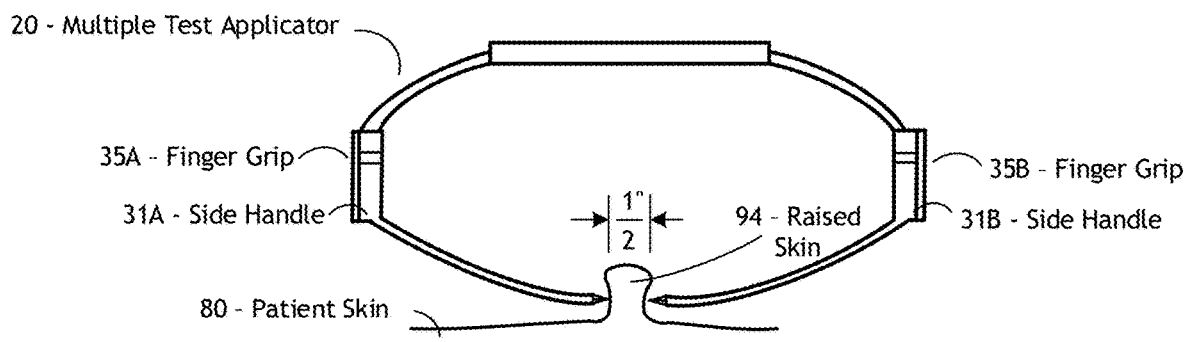
FIG. 8B is a front view of the multiple test applicator of FIG. 5, the multiple test applicator now being in a compressed state, the pair of opposed scratching barbs resting upon the skin of a patient with each of the scratching barbs disposed at two test sites, with the skin positioned between the opposed scratching barbs having been lifted upwards.
Figure 8C:
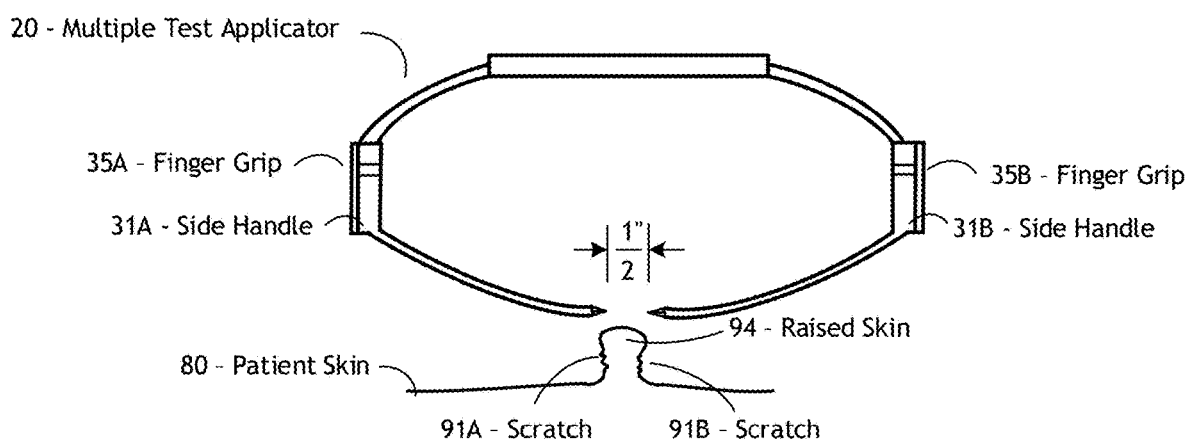
FIG. 8C is a front view of the multiple test applicator of FIG. 5, the multiple test applicator still being in a compressed state, the pair of opposed scratching barbs now being raised from the skin of the patient with scratches now appearing on each side of the raised skin of the patient.

FIGS. 8A, 8B, and 8C depict the first preferred embodiment of the multiple test applicator [10] of the present invention during allergy barb deposition.

FIG. 8A is a front view of the multiple test applicator [10] in an expanded position, with the scratching barbs [61A and 61B] resting upon the skin of a patient [80]. The scratching barbs [61A and 61B] each include a trace of their respective allergens and are prepared for allergen deposition.

FIG. 8B depicts a front view of the multiple test applicator [10]. The multiple test applicator [10] is now in a compressed position by use of the pair of finger grips [35A and 35B]. The pair of scratching barbs [61A and 61B] are resting upon the skin of the patient [80] and positioned about a portion of the raised skin [94] that has been lifted upwards [94] between the pair of opposed pair of scratching barbs [61A and 61B]. The multiple test applicator [10] is in the allergen deposition position [92].

FIG. 8C is a front view of the multiple test applicator [10]. The multiple test applicator [10] is still being compressed. The pair of scratching barbs [61a and 61B] now have been raised upward from the skin of the patient [80] with a pair of scratches [91A and 91B] now appearing on each side of the portion of the skin of the patient that was lifted upwards [94].

The multiple test applicator [10] comprises a first scratching barb [61A] secured to a first side handle [31A], and a second scratching barb [61B] secured to a second side handle [31B].

The first scratching barb [61A] is cooperatively engaged with a first reservoir [51A] on a fluid tray [50] during allergen loading. A first allergen [71] is retainable in the first reservoir [51A]. The first scratching barb [61A] retains some of the first allergen [71] when removed from the first reservoir [51A] during the allergen loading.

The first and second scratching barbs [61A and 61B] are each projecting in an upward direction away from the fluid tray [50].

The second scratching barb [61B] is cooperatively engaged with a second reservoir [51B] in the fluid tray [50] during the allergen loading. The second scratching barb

[61B] opposes the first scratching barb [61A]. The second scratching barb [61B] cooperatively engages with the first scratching barb [61A]. A second allergen is retainable in the second reservoir [51B]. The second scratching barb [61B] retains some of the second allergen [71] when removed from the second reservoir [51B] during the allergen loading.

When subsequently repositioned upon the skin of the patient [80], the scratching barbs [61A and 61B] contact both sides of the raised portion of the skin [94] of the patient. The skin of the patient [80] is raised by the pair of skin lifting pads [45A and 45B], one positioned on each side of each scratching barb [61A and 61B]. Also, the skin lifting pads [45A and 45B] are positioned relative to each scratching barb [61A and 61B] to limit the depth that each scratching barb [61A and 61B] penetrates the skin of the patient [80].

The first side handle [31A] is secured to the first scratching barb [61A] and the second side handle [31B] is secured to the second scratching barb [61B]. The first side handle [31A] opposes the second side handle [31B]. The first side handle [31A] cooperatively engages with the second side handle [31B] such that when inward pressure is applied by an operator holding in one hand the first and second side handles [31A and 31B] during allergen deposition the first scratching barb [61A] is caused to move substantially in a lateral direction across a first section of skin [81A] as the second scratching barb [61B] is caused to move substantially in a lateral direction across a second section of skin [81B] toward the first scratching barb [61A].

The first scratching barb [61A] and the second scratching barb [61B] cooperatively engage to grasp some of the skin of the patient [80]. The first scratching barb [61A] generates a first scratch [91A] and deposits a portion of the first allergen [71] into the first scratch [91A] preferably within the first section of the skin of the patient [81A] as the second scratching barb [61B] generates a second scratch [91B] depositing a portion of the second allergen [71] into the second scratch [91B] preferably within the second section of the skin of the patient [81B].

Then, the multiple test applicator [10] of the present invention is then pulled up and away from the skin of the patient [80]. The operator then waits between 10 to 20 minutes to determine how the patient has reacted to each of these allergens [71]. After the testing has been completed, the physician analyzes the test results to determine the next course of treatment.

With the scratching barbs [61A and 61B] now positioned on the skin of the patient [80], the multiple test applicator [10] is moved from the relaxed state to the compressed state. In so doing, the scratching barbs [61A and 61B] will break the skin of the patient [80] and generate a plurality of small scratches [91A and 91B]. A trace amount of each allergen [71] has been retained on each scratching barb [61A and 61B] and is inserted into each scratch [91A and 91B] on the skin of the patient [80].

The applicator [10] of the present invention for administering the plurality of allergens uses the multiple test system [20] requires allergen loading (the position [25] is depicted in DETAIL "A" of FIG. 5) and allergen deposition (the position [92] is depicted in FIG. 7).

Figure 9A:
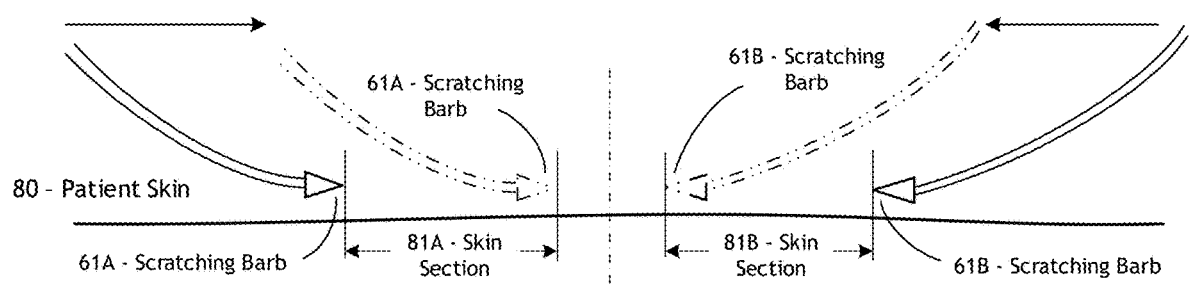
FIG. 9A depicts an exploded view of the first preferred embodiment of the multiple test applicator of the present invention with the scratching barbs pointed upward away from the bottom of fluid tray of the multiple test applicator of FIG. 5 as the first and second scratching barbs are positioned upon the skin of the patient in the expanded state, with the compressed state of the first and second scratching barbs shown in phantom.
Figure 9B:
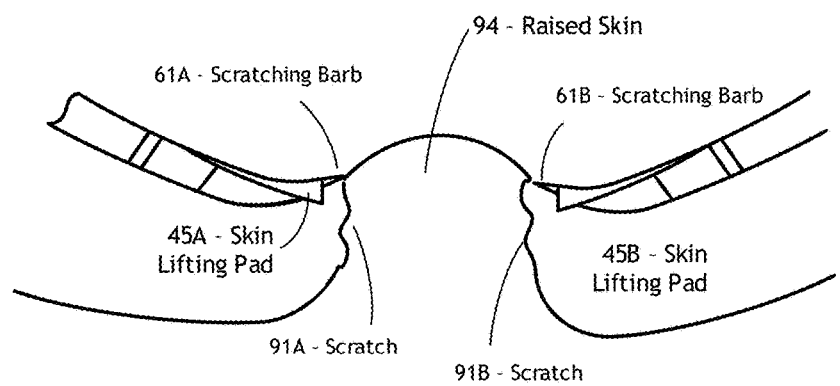
FIG. 9B depicts an exploded side view of a pair of scratching barbs being depicted in the compressed state as the scratching barbs are being raised upward on a portion of the skin of a patient that has been pulled together as the scratching barbs generate a pair of scratches, a pair of skin lifting pads being positioned, one on each side of each skin scratching barb, the skin lifting pads lifting the skin and limiting the depth of the penetration of the scratching barb.

FIG. 9A depicts an exploded view of the first preferred embodiment of the multiple test applicator [10] of the present invention with the scratching barbs pointed upward away from the fluid tray of the multiple test applicator [10]. The first scratching barb [61A] and the second scratching barb [61B] are positioned upon the skin of the patient [80] in the expanded state, with the compressed state of the first scratching barb [61A] and the second scratching barb [61B] shown in phantom. As the first scratching barb [61A] moves substantially in a lateral direction across a first section of the skin [81A] the second scratching barb [61B] moves substantially in a lateral direction across a second section of the skin [81B] toward the first scratching barb [61A]. As depicted in FIG. 9B, the first scratch [91A] is preferably generated in the first section of the skin [81A] as the second scratch [91B] is preferably generated in the second section of the skin [81B].

FIG. 9B depicts an exploded side view of a pair of scratching barbs [61A] being raised upward on a portion of the skin of a patient [80] that has been pulled together and raised [94] as a pair of scratches [91A and 91B] from the pair of scratching barbs [61A and 61B] have been generated. Skin lifting pads [45A and 45B] are shown on both sides of the scratching barb [61A and 61B], that lift the skin and limit the depth of penetration of the scratching barb [61A and 61B].

The multiple test applicator [10] including the scratching barbs [61A and 61B] is subsequently transferred to the skin of the patient [80]. Once the multiple test applicator [10] is on the skin of the patient [80], the applicator [10] is moved in such a way as to lift the skin in front of the scratching barbs [61A and 61B]. The next action is to lift the multiple test applicator [10] perpendicular to the skin of the patient [80], causing the scratching barbs [61A and 61B] containing a trace amount of allergen [71], to scratch the skin through the epidermis in a way so not to penetrate the dermis.

The first side handle cooperatively engages with the second side handle such that application of inward pressure on said first side handle and said second side handle during allergen deposition causes the first scratching barb [61A] to move in a lateral direction across a first section of skin [81A] as the second scratching barb [61B] moves in a lateral direction across a second section of skin [81B] towards the first scratching barb as the multiple test applicator [20] moves from a relaxed state to a compressed state.

Figure 10:
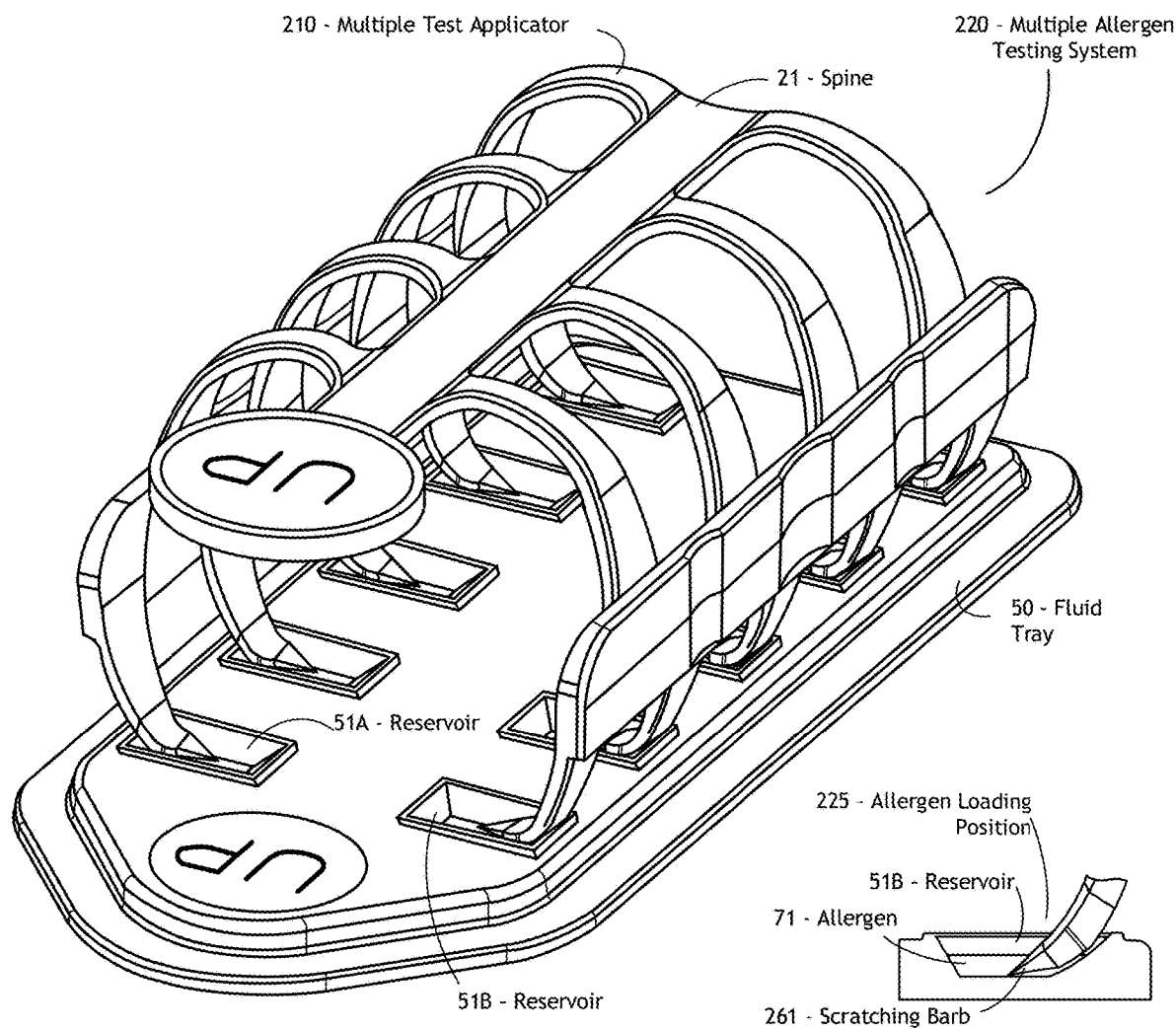
FIG. 10 depicts an assembly view of a second preferred embodiment of the multiple allergen testing system for use in the automated office system of the present invention comprising a second preferred embodiment of the multiple test applicator having ten scratching barbs cooperatively engaged with ten reservoirs of a fluid tray, the multiple test applicator being positioned on the fluid tray; and DETAIL "B" depicts an exploded side view of the scratching barb positioned in the reservoir of the fluid tray pointing downward toward the bottom to the fluid tray, the reservoir being partially filled with allergen.
Figure 11A:
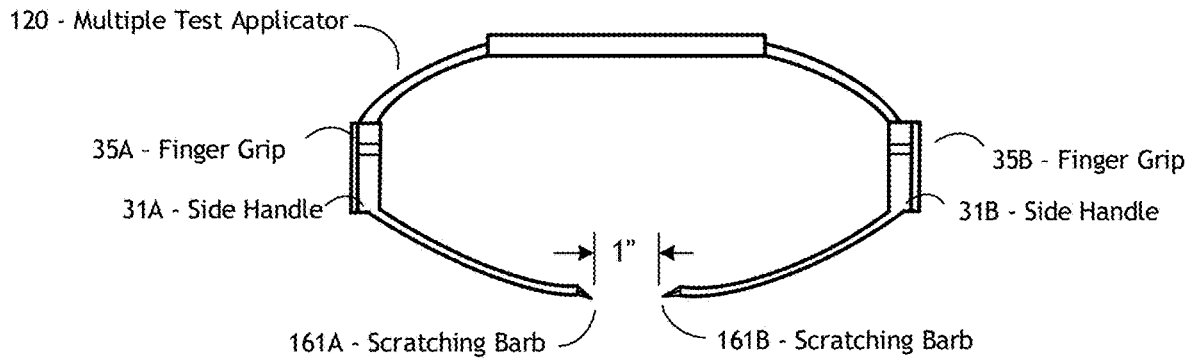
FIG. 11A is a front view of the multiple test applicator of FIG. 10 in a relaxed state, the scratching barbs now being loaded, and each scratching barb including a trace of their respective fluids and are now prepared for allergen deposition.
Figure 11B:
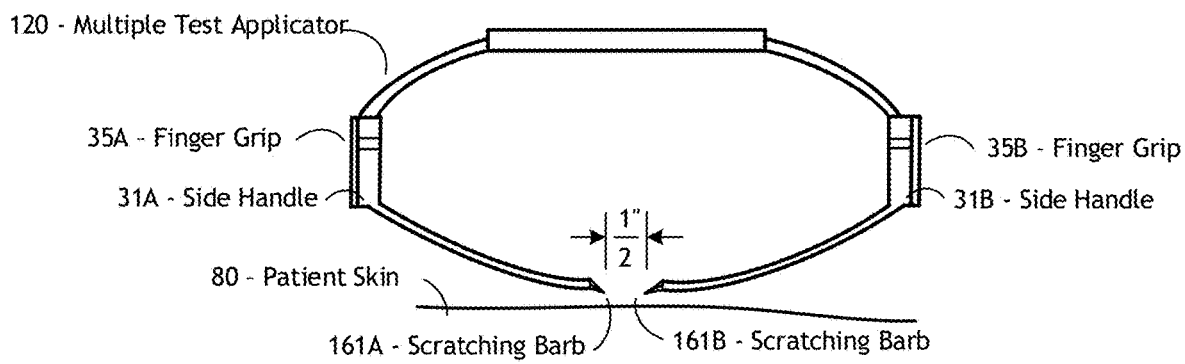
FIG. 11B is a front view of the multiple test applicator of FIG. 11A in a compressed state resting on the skin of a patient, The scratching barbs are resting upon the skin of a patient with each of the two scratching barbs pointed downward.
Figure 11C:
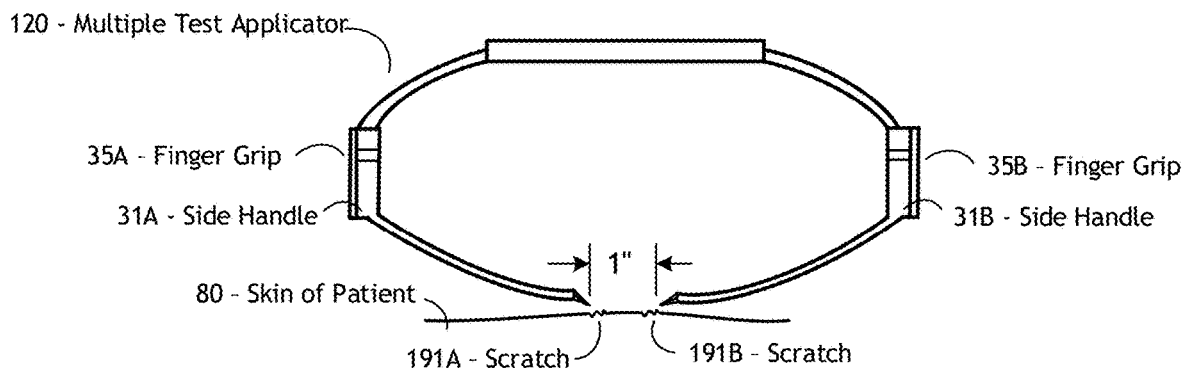
FIG. 11C is a front view of the multiple test applicator of FIG. 11B in an expanded state, the scratching barbs now have generated a pair of scratches at a pair of test sites as the scratching barbs have separated from each other.
Figure 12:
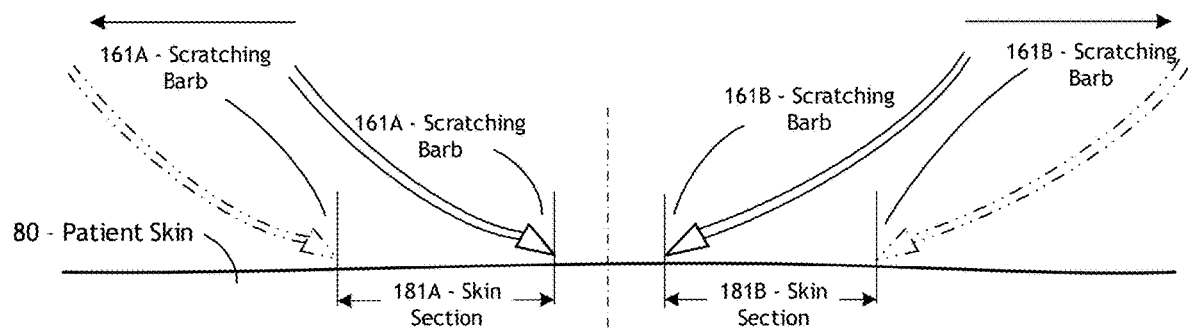
FIG. 12 depicts an exploded view of the second preferred embodiment of the multiple test applicator of the present invention with the scratching barbs pointed downward toward the fluid tray of the multiple test applicator of FIG. 10 as the first and second scratching barbs are positioned upon the skin of the patient in the compressed state and slight pressure is applied as the compression is released, the first and second scratching barbs shown in phantom after release.

FIG. 10-12 disclose a second preferred embodiment of the multiple test applicator [110] of the present invention for allergy skin testing.

FIG. 10 depicts an assembly view of a second preferred embodiment of multiple allergen testing system [120] comprising of a second preferred embodiment of the multiple test applicator [110] including a first scratching barb [161A] in cooperative engagement a first fluid reservoirs [51A] and a second scratching barb [161B] in cooperative engagement with a second fluid reservoir [51B] both fluid reservoirs [51A and 51B] positioned in a fluid tray [50].

DETAIL "B" depicts an exploded side view of the scratching barb [161B] positioned in a reservoir [51B] of the fluid tray [50] while in the allergen loading position. The reservoir [51B] is partially filled with allergen [71]. Here, the scratching barbs [161A and 161B] project in a downward direction pointing to the bottom of the fluid tray [50]. The multiple test applicator [110] is enabled to reposition from the compressed state to the relaxed state when placed on the skin of the patient [80] during allergen deposition [92].

The multiple test applicator [110] comprises a first scratching barb [261A] secured to a first side handle [31A], and a second scratching barb [161B] secured to a second side handle [31B].

The first scratching barb [161A] is cooperatively engageable with a first reservoir [51A] on a fluid tray [50] during allergen loading. A first allergen [71] is retainable in the first reservoir [51A]. The first scratching barb [161A] retains some of the first allergen [71] when removed from the first reservoir [51A] during the allergen loading.

The second scratching barb [161B] is cooperatively engageable with a second reservoir [51B] in the fluid tray [50] during the allergen loading. The second scratching barb [161B] opposes the first scratching barb [161A]. The second scratching barb [161B] cooperatively engages with the first scratching barb [161A]. A second allergen [71] is retainable in the second reservoir [51B]. The second scratching barb [161B] retains some of the second allergen [71] when removed from the second reservoir [51B] during the allergen loading.

The first side handle [31A] secured to the first scratching barb [161A] and a second side handle [31B] secured to the second scratching barb [161B]. The first side handle [31A] opposes the second side handle [31B]. The first side handle [31A] cooperatively engages with the second side handle [31B] as inward pressure is applied by an operator holding in one hand the first side handle [31A] and the second side handle [31B] after the allergen loading is completed and prior to the allergen deposition. The first scratching barb [161A] and the second scratching barb [161B] are placed on skin of the patient [80]. The inward pressure is then released during the allergen deposition such that the first scratching barb [161A] moves substantially in a lateral direction across a first section of the skin of the patient [181A] as the second scratching barb [161B] moves substantially in a lateral direction across a second section of the skin of the patient [181B] away from the first scratching barb [161A]. The first scratching barb [161A] generates a first scratch [191A] depositing a portion of the first allergen [71] into preferably a first section of skin [181A] the first scratch [191A] as the second scratching barb [161B] generates a second scratch [191B] depositing a portion of the second allergen [71] preferably into preferably a second section of skin [181B] of the second scratch [191B].

FIGS. 11A, 11B, and 11C depict the first preferred embodiment of the multiple test applicator [110] of the present invention during allergy barb deposition [92]. Each of the scratching barbs [161A or 161B] of the multiple test applicator [120] are pointing downward toward the bottom of the fluid tray [50] when disposed in the fluid tray [50]. Again, the fluid tray [50] contains multiple allergens, generally test fluid in each reservoir [51A and 51B]. Allergens [71] are initially selected and placed into containment reservoirs [51A and 51B] in the fluid tray [50], and care is taken not to use an excess amount of the allergens. After allergen loading is completed, the operator lifts the multiple test applicator [120] out of the fluid tray [50], the multiple test applicator [110] being in the relaxed state. Using the pair of opposing finger grips [35A and 35B], the operator applies pressure moving the multiple test applicator [120] to a compressed state before placing the applicator [120] upon the skin of the patient [80] in the allergen deposition position, the operator pushes lightly upon the applicator [220] and slowly releases the finger grips [35A and 35B]. This generates a pair of scratches [191A and 191B] at each test site essentially simultaneously on the skin of the patient [80]. Trace amounts of each respective allergen [71] then seep into each respective scratch [191A or 191B]. The use of the finger grips [35A and 35B] to move the multiple test applicator [120] from the relaxed state to the compressed state and then back again to the relaxed state enables one-handed operation by the operator. Then, the multiple test applicator [120] is pulled up and away from the skin of the patient [80].

FIG. 11A is a front view of the multiple test applicator [110] in an expanded position, with the scratching barbs [161A and 161B] resting upon the skin of a patient [80]. The scratching barbs [161A and 161B] each include a trace of their respective allergens and are prepared for allergen deposition.

After allergen loading is completed, the operator lifts the multiple test applicator [120] out of the fluid tray [50], the multiple test applicator [110] being in the relaxed state. Using the pair of opposing finger grips [35A and 35B], the operator applies pressure moving the multiple test applicator [120] to a compressed state before placing the applicator [120] upon the skin of the patient [80] in the allergen deposition position, the operator pushes lightly upon the applicator [120] and slowly releases the finger grips [35A and 35B].

FIG. 11B depicts a front view of the multiple test applicator [110] now in a compressed state by use of the pair of finger grips [35A and 35B]. The pair of scratching barbs [161A and 161B] are resting upon the skin of the patient [80] and positioned upon the skin of the patient [80] and released.

FIG. 11C is a front view of the multiple test applicator [110]. As the pair of scratching barbs [161A and 161B] are released to a relaxed state, the first scratching barbs [161A] has generated a first scratch [191A] as the second scratching barb [161B] has generated a second scratch [191B]. A first scratch [191A] is preferably generated in a first section of the skin [181A] as the second scratch [191B] is generated in the second section of the skin [181B].

Then, the operator waits between 15 to 20 minutes to determine how the patient has reacted to these allergens. After the testing has been completed, the physician analyzes the test results to determine the next course of treatment.

FIG. 12 depicts an exploded view of the second preferred embodiment of the multiple test applicator of the present invention [220] with the scratching barbs pointed downward toward the fluid tray of the multiple test applicator of FIG. 10 as the first and second scratching barbs are positioned upon the skin of the patient. The multiple test applicator of the present invention [220] is initially in the compressed state and slight pressure is applied as the applicator [220] is positioned on the skin of the patient as the compression is released. The first and second scratching barbs are shown in phantom after release. The first scratch formed on the first skin section [181A] and the second scratch formed on the second skin section [181B] are formed simultaneously and are the same size.

The next action is to lift the multiple test applicator [220] perpendicular to the skin of the patient [80], causing the scratching barbs [161A and 161B] containing a trace amount of allergen [71], to scratch the skin through the epidermis in a way so not to penetrate the dermis.

The first side handle cooperatively engages with the second side handle such that application of inward pressure on said first side handle and the second side handle during allergen deposition causes the first scratching barb [161A] to move in a lateral direction across a first section of skin [181A] as the second scratching barb [161B] moves in a lateral direction across a second section of skin [181B] away from the first scratching barb.

In the allergen deposition position, the multiple test applicator [20] is compressed, and each allergen [57] is deposited into each respective scratch [91] generated by each respective scratching barb on the skin of the patient [90] for further analysis as needed by the treating physician.

After the prescribed time between 15 to 20 minutes the test operator records the skin condition with an evaluation form or a photo of each scratch site. The applicator includes break-off features for the arms, legs, and tips enabling more efficient disposal of the device after use with a patient. The break-off features for the tips enable this part of the applicator to be disposed of in a biohazard sharps container. The leg break-off points enable the legs to be broken off from the spine and the legs and spine to be disposed of in a separate container from the tips. The fluid tray can also be disposed of in the same container. This increases the packing density of the discarded material and a much lower disposal cost.

Also, the multiple test applicator [20] of the multiple allergen testing system [10] has the advantage of breaking the skin of the patient without downward pressure. This diminishes chances of the mast cells (histamine containing cells) releasing the histamine secondary to pressure causing a false positive. This is a critical factor with percutaneous allergy testing.

The single and multiple allergen testing system [110] enables testing for a single allergy or multiple allergies in the same device. The allergen testing applicator [120] simulates the best practice in a controlled procedure. The multiple-allergen testing system is designed around a multiple allergen testing system [120] that enables the accurate and repeatable placement of allergy testing fluid, either in a tray or on the skin of a patient. The testing procedure also controls the scratching or pricking of the skin, to introduce the allergen in a more controlled manner.

The multiple test applicator [20] and the fluid tray [50] are preferably made of engineering grade polymers that are sterilized prior to use in an autoclave, or other standard sterilization procedures. Hence, the materials preferably are made of plastics that are stable at higher temperatures. The multiple test applicator [20] is depicted having ten scratching barbs. The multiple applicator unit may also have two, four, six, eight, twelve, and any of a wide variety of configurations, as needed.

It is critical during use that the allergens for the various reservoirs [54] do not become intermixed as this contamination will affect the test results. The suggested minimum distance between two neighboring scratching barbs extending from the same side frame is preferably at least three-quarters of an inch.

It is critical that the multiple test applicator unit be held in one hand of the medical technician who is administering the test. This will enable the other hand to be free to take notes, to assist the patient, or do whatever becomes necessary during the administration of the procedure.

Accordingly, the multiple test applicator [20] preferably has ten scratching barbs as depicted and is preferably about 2" (height)×2" (width)×5" (length). If the multiple test applicator has eight scratching barbs (2×4), the length is preferably 3.75" to 4.50" in length, if the multiple test applicator has twelve scratching barbs (2×6), the length is about 5.00 to 5.50", etc. It is to be understood that while the multiple allergen testing device as depicted in the accompanying drawings depicts a unit with ten testing devices, one skilled in the art can readily modify this geometry to include 4, 6, 8, 12, 16, 20, or any other combination of multiple testing devices, this disclosure is being limited to 10 for purposes of illustration only.

The multiple test applicator [20] enables testing for multiple allergies in one device and one test procedure or one test with the single tester and one allergy testing fluid. The most consistent results have been achieved by inserting a drop of allergy testing fluid on the skin and then scratching the skin with a simple needle (best practice). The multiple test applicator [20] duplicates the best practice but in a controlled, repeatable, and reproducible way. The system built around the devices enables the accurate and repeatable placement of the allergy testing fluid, in a tray and transfers this fluid to the multiple test applicator [20] or the single test applicator [180], by placing the testing end of the device, into the fluid tray [50]

After the prescribed time between 15 to 20 minutes the medical technician records the skin condition. The applicator includes break-off features for the arms, legs, and tips enabling more efficient disposal of the device after use with a patient. The break-off features for the tips enable this part of the applicator to be disposed of in a biohazard sharps container. The leg break-off points enable the legs to be broken off from the spine and the legs and spine to be disposed of in a separate container from the tips.

The fluid tray [50] can also be disposed of in the same container. This increases the packing density of the discarded material and a much lower disposal cost.

Also, the multiple test applicator [20] has the advantage of breaking the skin of the patient [90] without downward pressure. This diminishes chances of the mast cells (histamine containing cells) releasing the histamine secondary to pressure causing a false positive. This may be a critical factor with percutaneous allergy testing.

Figure 13A:
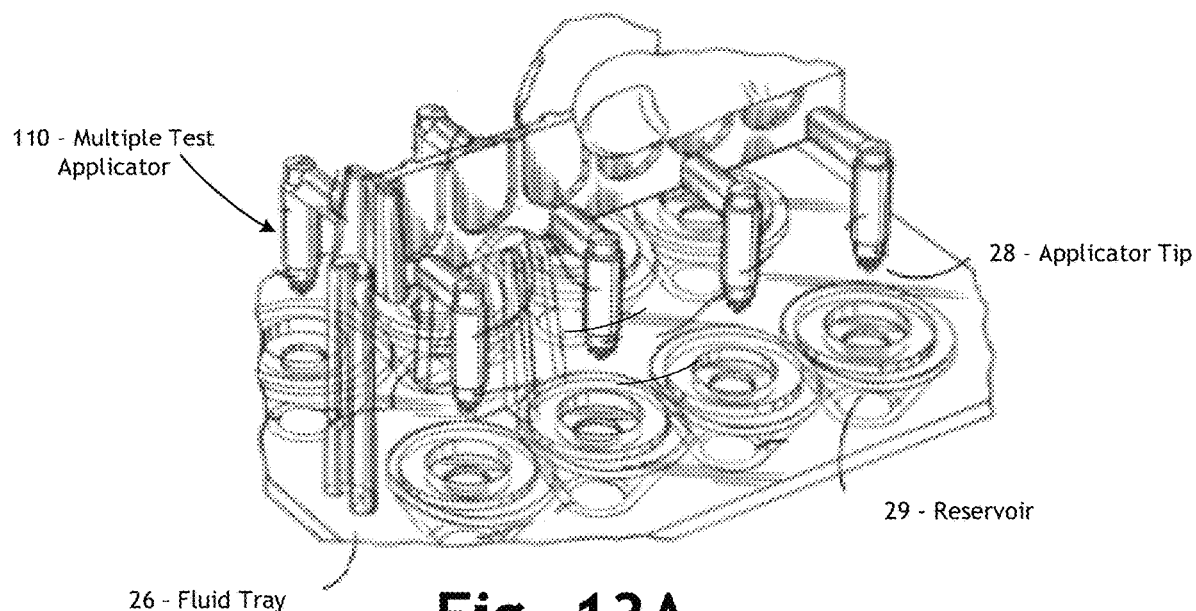
FIG. 13A depicts a prior art allergy testing system comprising a multiple applicator unit disposed relative to a fluid tray. The multiple applicator unit has a grip portion for holding the device. One or more legs extend from the grip portion, and each leg is oriented to interact with a reservoir containing a potential allergen. Each leg has a test head, and each test head has a plurality of elongated spike members. The elongated spike members have a sharp end configured to receive the potential allergen from a well and to puncture the skin of the patient being tested.

FIG. 13A depicts a prior art allergy testing system comprising a multiple test applicator [110] disposed relative to a fluid tray [54]. Each applicator tip [59] of the multiple test applicator [110] is shown in a loading position and positioned in a reservoir [56]. The multiple test applicator [110] is known in the prior art (see U.S. Pat. No. 8,469,900). The multiple test applicator [110] is lowered in a vertical direction and pressed against the skin of the patient.

The multiple test applicator is preferably either a "prick tester" or a "scratch tester". Some examples of a "prick tester" are U.S. Pat. No. 9,788,780 (Smollar) entitled "Allergy Skin Test Applicator, and Related Testing Tray, Testing Kit and Testing Method"; U.S. Pat. No. 8,469,900 (Hein, Jr., et al.) entitled "Allergy Testing Device and Method of Testing for Allergies"; U.S. Pat. No. 5,738,108 (Hein), entitled "System for Multi-Site Skin Testing and Components Thereof".

Figure 13B:
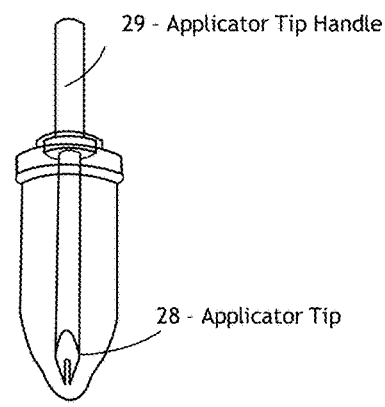
FIG. 13B depicts a prior art prick device that is compatible with a multiple applicator unit and a fluid tray. The prick device is lowered in a vertical direction and pressed against the skin of the patient. The elongated spike members have a sharp end configured to receive the potential allergen from a well and to puncture the skin of the patient being tested.

FIG. 13B depicts another prior art puncture device (see U.S. Pat. No. 7,631,765) that is compatible with a multiple applicator unit and a fluid tray. Each puncture tip [28] includes a puncture tip handle [29].

Figure 14A:
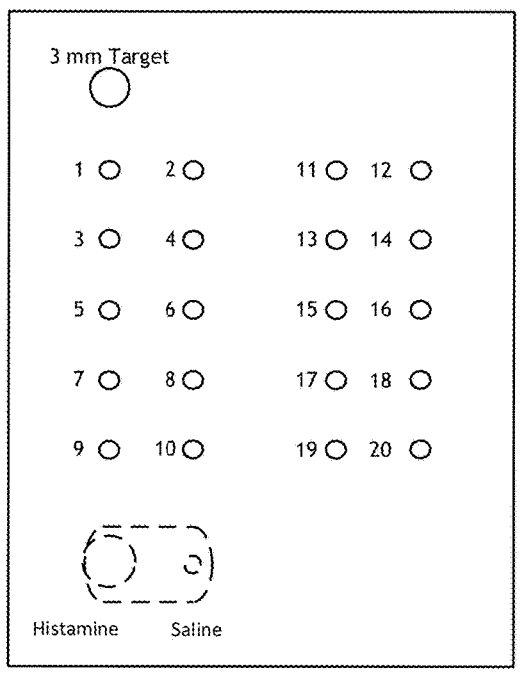
FIG. 14A depicts a simplified sketch of the first photo of the skin of the patient (back, arm, or leg) taken immediately after allergen insertion at the twenty sites (four rows of five), including a 3 mm target at the top left corner, and control fluids of a histamine and saline solution at the bottom.

FIG. 14A depicts a simplified drawing of the first photo of the skin of the patient (back, arm, or leg) taken immediately after allergen insertion at the twenty sites (four rows of five), including a 3 mm target at the top left corner, and control fluids of a histamine and saline solution at the bottom.

Figure 14B:
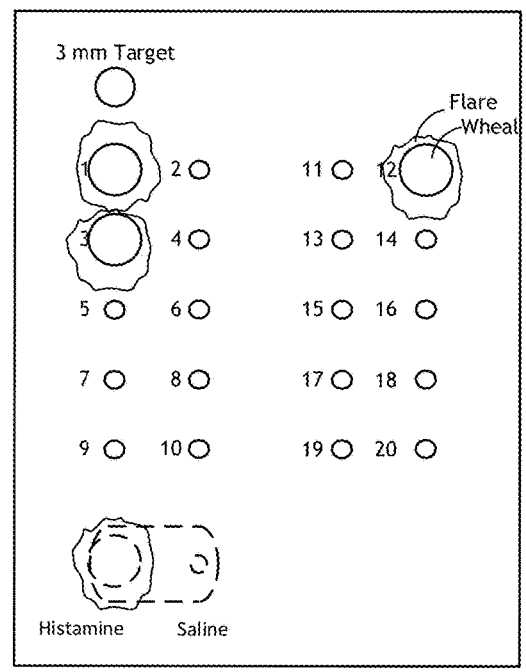
FIG. 14B depicts a simplified sketch of the second photo of the skin of the patient (back, arm, or leg) taken 15 to 20 minutes after the first photo of the twenty sites (four rows of five), including a 3 mm target at the top left corner, and control fluids of a histamine and saline solution at the bottom. Wheals and flares have formed at sites 1, 3, and 12, as well as the site of the histamine fluid insertion.

FIG. 14B depicts a simplified drawing of the second photo of the skin of the patient (back, arm, or leg) taken 15 to 20 minutes after the first photo of the twenty sites (four rows of five), including a 3 mm target at the top left corner, and control fluids of a histamine and saline solution at the bottom. Wheals and flares have formed at sites 1, 3, and 12, as well as the site of the histamine fluid insertion.

A hypothetical example of one of the aspects of the automated office and machine learning algorithm evaluation of skin testing wheals and flares, as well as their interpretation. FIG. 14A depicts the skin of a patient, either on the back or arm, with typical allergy skin tests, immediately after a series of tests have been performed. The skin tests show groupings, as an example, grass 1, grass 2, tree 1, tree 2 may be used and the control, saline and histamine. In addition to the specific tests, a 3 mm target is applied to the skin. At this point, the virtual reality or augmented reality viewing device takes a picture of the skin and transmits the image to the smart database. The 3 mm target is a reference sizing target that enables an augmented algorithm to calculate the size of each of the skin testing wheals. This target allows for measurements to be calculated regardless of the distance, away from the skin, that the device is, when taking the picture. This is accomplished by the algorithm knowing the diameter of the target and also knowing the distance the device is from the skin. The distance from the skin can be measured by, for example, a LIDAR system built into the device. However, any other electronic distance measuring system (or manual measuring system) can be used. At this point the algorithm takes the picture of the skin, immediately after the tests have been performed and with the knowledge of the size of the target, calculates the size of each of the allergy test sites. After 15 to 20 minutes has elapsed, a second picture of the test site is taken, as shown in FIG. 14B. This second picture is sent to the smart database. The algorithm for the virtual reality or augmented reality viewing device calculates the size of each wheal and each flare and compares this second set of measurements to the first set of measurements. If the wheals change their size and if a flare is present, the algorithm will determine if a positive or negative skin reaction has occurred and will grade the reaction as, for example, an "0" to "4+". Typically, an "0" means no change in wheal size and no red flare is present. A "4+" typically means that the wheal has grown by more than 3 mm and a large red flare is present. This grading system can be adjusted as the medical profession learns more about allergy testing. It will also be modified, immediately, by the doctor changing/correcting the scoring from the algorithm. As the data from a large number of medical professionals are used to change or correct the smart database and algorithm, the automated testing results will continue to become more accurate. In addition, other factors that will improve the calculation and reporting results of the algorithm are the testing of patients with various skin tones and the rejection of tattoos on or near the testing area.

FIG. 15 depicts the "Fitzpatrick Skin Tone Scale" with the six basic skin types, and the Typical Features and the Reactions to the Sun commonly associated with each basic skin type. is a numerical classification schema for human skin color. The scale was developed to estimate the response of different types of skin to ultraviolet (UV) light. The scale was initially developed on the basis of skin color to measure the correct dose of UVA for PUVA, and when the initial testing based only on hair and eye color resulted in too high UVA doses for some, it was altered to be based on the patient's reports of how their skin responds to the sun; it was also extended to a wider range of skin types. The scale remains a recognized tool for dermatological research into human skin pigmentation.

The viewing device [12] that the medical professional uses to view the allergy tests, on the skin of the patient, is a virtual reality headset or an augmented reality device. The viewing device [12] can also be a smart phone or a tablet computer. The viewing device [12] uses its internal camera to view the skin of the patient and overlays the results on the live view of the test sites of the skin of the patient. The results provide a positive or negative result to the allergy test, as determined by the current knowledge that the machine learning system has. That knowledge is the algorithm that evaluates wheals and flares and determines which are positive and which are negative. The data that the algorithm uses as well as how the algorithm uses the data will be automatically modified by the evaluation of the medical professional positive or negative results defined by the algorithm.

Allergy tests are administered to the skin of a patient. The viewing device [12] takes a photograph of the test sites. This photograph is sent to a computer that stores the image of the test sites. Software and the data, that are the algorithm, look at the initial photograph and sets certain parameters that define the size and shape of the wheals under the skin of the patient. After about 15 minutes, a second photograph is taken, with that picture being sent to the computer that stores the first picture and its definition of the original size and shape of the wheals. The size, shape, and color, as well as temperature, of the wheals, in the second picture are analyzed and defined. The data in the second picture is compared to the data in the first picture and positive or negative results are determined by the software (algorithm). This determination is made based on the software (algorithm's) knowledge of how much larger the wheal has grown and how the color or flare has changed from the first picture when compared to the second picture. When the medical professional looks at the positive or negative results of each test, as defined by the software's algorithm (programming and initial data) he/she can change the positive or negative results that the software (algorithm) generated. This change is incorporated into the software such that future analysis will learn from the judgment and knowledge of the medical professionals.

Initially, the machine learning software will be loaded with medical standard data on wheals and flares, including pictures. This includes the size, shape and color changes of the wheals and flares undergoing a positive reaction as well as the minimal changes when showing a negative reaction. Also included are pictures of tattoos, moles, and other skin conditions, such as rashes that are common to human skin. A skin tone or pigment concentration of a patient, as defined on a scale such as the "Fitzpatrick Skin Tone Scale", are added (see FIG. 15). Also included is the current medical definition as to what constitutes a positive or negative reaction. Naturally, the reactions to saline and histamine, as controls, will also be added.

As more and more medical professionals use the system, their combined knowledge and experience enables the system and the machine learning to improve over time at defining what is a positive and what is a negative reaction. Machine learning improves with time and is even applicable to other medical specialties, such as dermatology and plastic surgery.

Still other objectives of the automated office system of the present invention will become apparent to those skilled in this art from the following description wherein there is shown and described in the preferred embodiment of this invention, simply by the way of illustration of the best modes contemplated for carrying out the present disclosure. As will be realized, the present disclosure is capable of different embodiments, and its several details are capable of modification in various, obvious aspects all without departing from the invention. Accordingly, the drawings and descriptions will be regarded as illustrative in nature and not as restrictive.

Throughout this application, various Patent Applications, PCT Applications, and Patents are referenced by number and inventor. The disclosures of these documents in their entireties are hereby incorporated by reference into this specification to more fully describe the state of the art to which this invention pertains.

It is evident that many alternatives, modifications, and variations of the automated allergy office of the present invention will be apparent to those skilled in the art in lieu of the disclosure herein. It is intended that the metes and bounds of the present invention be determined by the appended claims rather than by the language of the above specification, and that all such alternatives, modifications, and variations which form a conjointly cooperative equivalent are intended to be included within the spirit and scope of these claims.

PARTS LIST

8. Automated Allergy Office System
10. Multiple Test Applicator—1$^{st}$ Embodiment
12. Augmented Reality Headset System
14. Machine Learning System
16. Electronic Medical Records
20. Multiple Allergen Testing System—1$^{st}$ Embodiment
21. Spine
25. Allergen Loading Position
26. Fluid Tray
28. Applicator Tip and
29. Applicator Tip Handle
31A and 31B. Side Handles
33A and 33B. Handle Arms
35A and 35B. Finger Grips
45A and 45B. Skin Lifting Pads
50. Fluid Tray
51A and 51B. Reservoirs
310. Multiple Test Applicator
56. Reservoir
59. Applicator Tip
61A and 61B. Scratching Barbs
71. Allergen
80. Patient Skin
81A and 81B. Skin Sections
91A and 91B. Scratches
93. Allergen Barb Depositing Position
94. Raised Skin
96. Operator Hand
110. Multiple Test Applicator—2$^{nd}$ Embodiment
120. Multiple Allergen Testing System—2$^{nd}$ Embodiment
161A and 161B. Scratching Barb
181A and 181B. Skin Sections
191A and 191B. Scratches
210. Multiple Test Applicator—3$^{rd}$ Embodiment

We claim:

1. An augmented reality automated allergy office method in the sequence set forth that selects a first test site and a second test site upon skin of a patient to configure treatment to address a first allergy condition of said patient, said augmented reality automated allergy office method comprising:
    a. delivering a trace amount of a first allergen to said first test site via a multiple test applicator as said multiple test applicator delivers a trace amount of a second allergen to said second test site during allergen deposition, said multiple test applicator being cooperatively engageable with a fluid tray during allergen loading, said multiple test applicator being cooperatively engageable with said skin of said patient during said allergen deposition;
    b. capturing a first image of said first test site and said second test site using a first smart phone or a first tablet computer;
    c. capturing a second image of said first test site and said second test site within 15 to 20 minutes after said allergen deposition with either said first smart phone or said first tablet computer or with a second smart phone or a second tablet computer, said second image being captured after said first image is captured, said first allergy condition being detectable as a first wheal forms at said first test site; and
    d. generating a computer-generated treatment plan using machine learning for said patient having said first allergy condition, said computer-generated treatment plan being a step-by-step procedure for a medical professional, said patient having an electronic medical record, said computer-generated treatment plan being stored in a medical database for treating patients with said first allergy condition.

2. The augmented reality automated allergy office method of claim 1, further comprising said computer-generated treatment plan including a manual override, said manual override being used to improve subsequent diagnostic and treatment procedures either for said patient or for another patient developing said first allergy condition.

3. The augmented reality automated allergy office method of claim 1, wherein said first image of said first test site and said second test site are captured after said allergen deposition.

4. The augmented reality automated allergy office method of claim 1, further comprising said multiple test applicator including a first and a second scratching barb, said first scratching barb opposing said second scratching barb, said first scratching barb moving in a lateral direction across a first section of said skin as said second scratching barb moves in a lateral direction across a second section of said skin.

5. The augmented reality automated allergy office method of claim 1, further comprising said multiple test applicator having an expanded state and a compressed state, a first side handle opposing a second side handle, said first side handle cooperatively engaging with said second side handle, said first side handle having a first scratching barb and said second side handle having a second scratching barb, wherein a squeezing together of said first side handle and said second side handle using only one hand decreases a distance between said first scratching barb and said second scratching barb.

6. The augmented reality automated allergy office method of claim 1, further comprising completing an analysis, the analysis being based upon a comparison of said first image of said first test site and said second test site with said second image of said first test site and said second test site for color and size changes to said first wheal.

7. The augmented reality automated allergy office method of claim 1, wherein said method is initiated in a home of said patient.

8. The augmented reality automated allergy office method of claim 1, further comprising said multiple test applicator having an expanded state and a compressed state, said multiple test applicator being in said expanded state during said allergen loading, and said multiple test applicator being in said compressed state during said allergen deposition.

9. An augmented reality automated allergy office method that selects a first test site and a second test site upon skin of a patient to configure treatment to address a first allergy condition of said patient, said augmented reality automated allergy office method comprising:
    a. providing a multiple test applicator that is cooperatively engageable with a fluid tray during allergen loading, said multiple test applicator being cooperatively engageable with said skin of said patient during allergen deposition, said multiple test applicator delivering a trace amount of a first allergen to said first test site as said multiple test applicator delivers a trace amount of a second allergen to said second test site during said allergen deposition;

b. capturing a first image of said first test site and said second test site using a first smart phone or a first tablet computer;

c. capturing a second image of said first test site and said second test site 15 to 20 minutes after said allergen deposition either with said first smart phone or said first tablet computer or a second smart phone or a second tablet computer, said first image of said first test site and said second test site being captured after said allergen deposition, said second image being captured after said first image is captured, said first allergy condition being detectable as a first wheal forms at said first test site; and d. generating a computer-generated treatment plan for treating said patient having said first allergy condition using machine learning, said computer-generated treatment plan being a step-by-step procedure for a medical professional, said patient having an electronic medical record, and said computer-generated treatment plan being stored in a medical database for treating patients with said first allergy condition.

10. The augmented reality automated allergy office method of claim 9, further comprising said multiple test applicator having an expanded position and a compressed position, a first side handle opposing a second side handle, said first side handle cooperatively engaging with said second side handle, said first side handle being cooperatively engaged with a first scratching barb and said second side handle being cooperatively engaged with a second scratching barb, wherein a squeezing together of said first side handle and said second side handle using only one hand decreases a distance between a first scratching barb and a second scratching barb.

11. The augmented reality automated allergy office method of claim 9, wherein said first image of said first test site and said second test site are captured after said allergen deposition.

12. The augmented reality automated allergy office method of claim 9, wherein an analysis at said first test site and said second test site is completed within 30 minutes of said allergen deposition.

13. The augmented reality automated allergy office method of claim 9, further comprising said computer-generated treatment plan including a manual override, said manual override being used to improve subsequent diagnostic and treatment procedures either for said patient or for another patient developing said first allergy condition.

14. The augmented reality automated allergy office method of claim 9, further comprising completing an analysis, the analysis being based upon a comparison of said first image of said first test site and said second test site with said second image of said first test site and said second test site for color and size changes to said first wheal.

15. The augmented reality automated allergy office method of claim 9, wherein said method is used to test for allergies to trees, grass, or mold.

16. The augmented reality automated allergy office method of claim 9, further comprising said multiple test applicator having an expanded state and a compressed state, said multiple test applicator being in said expanded state during said allergen loading, and said multiple test applicator being in said compressed state during said allergen deposition.

17. An augmented reality automated allergy office method that selects a first test site and a second test site upon skin of a patient to configure treatment to address a first allergy condition of said patient, said augmented reality automated allergy office method comprising:

a. providing a multiple test applicator that is cooperatively engageable with a fluid tray during allergen loading, said multiple test applicator being cooperatively engageable with said skin of said patient during allergen deposition, said multiple test applicator delivering a trace amount of a first allergen to said first test site as said multiple test applicator delivers a trace amount of a second allergen to said second test site during said allergen deposition;

b. capturing a first image of said first test site and said second test site using a first smart phone or a first tablet computer;

c. capturing a second image of said first test site and said second test site 15 to 20 minutes after said allergen deposition either with said first smart phone or said first tablet computer or with a second smart phone or a second tablet computer, said second image being captured after said first image has been captured, said first allergy condition being detectable as a first wheal forms at said first test site, completing an analysis, the analysis being based upon a comparison of said second image of said first test site and said second test site with said first image of said first test site and said second test site for color and size changes to said first wheal; and d. generating a computer-generated treatment plan for said patient having said first allergy condition using machine learning, said patient having an electronic medical record, said computer-generated treatment plan being a step-by-step procedure for a medical professional, and said computer-generated treatment plan being stored in a medical database for treating patients with said first allergy condition.

18. The augmented reality automated allergy office method of claim 17, further comprising said multiple test applicator having an expanded position and a compressed position, a first side handle opposing a second side handle, said first side handle cooperatively engaging with said second side handle, said first side handle being cooperatively engaged with a first scratching barb and said second side handle being cooperatively engaged with a second scratching barb, wherein a squeezing together of said first side handle and said second side handle using only one hand decreases a distance between a first scratching barb and a second scratching barb.

19. The augmented reality automated allergy office method of claim 17, further comprising said multiple test applicator having an expanded position and a compressed position, a first scratching barb opposing a second scratching barb, said first scratching barb being positioned nearer said second scratching barb in said compressed position, said first scratching barb being positioned farther from said second scratching barb in said expanded position.

20. The augmented reality automated allergy office method of claim 17, wherein said analysis at said first test site and said second test site is completed within 30 minutes of said allergen deposition.

21. The augmented reality automated allergy office method of claim 17, further comprising said computer-generated treatment plan including a manual override, said manual override being used to improve subsequent diagnostic and treatment procedures either for said patient or for another patient developing said first allergy condition.

22. The augmented reality automated allergy office method of claim 17, further comprising said multiple test applicator including a first and a second scratching barb, said first scratching barb opposing said second scratching barb, said first scratching barb moving in a lateral direction across a first section of said skin as said second scratching barb moves in a lateral direction across a second section of said skin, said first scratching barb being generating a first scratch depositing said trace amount of said first allergen into said first scratch as said second scratching barb generates a second scratch depositing said trace amount of said second allergen into said second scratch.

23. The augmented reality automated allergy office method of claim 17, wherein said method is used to test for allergies to trees, grass, or mold.

24. The augmented reality automated allergy office method of claim 17, further comprising said multiple test applicator having an expanded state and a compressed state, said multiple test applicator being in said expanded state during said allergen loading, and said multiple test applicator being in said compressed state during said allergen deposition.

* * * * *